(12) United States Patent
Li et al.

(10) Patent No.: US 11,311,368 B2
(45) Date of Patent: Apr. 26, 2022

(54) DEVICE FOR PRINTING LUMEN TISSUE CONSTRUCT, METHOD FOR USING THE SAME AND 3D BIOPRINTER

(71) Applicant: Revotek Co., Ltd, Sichuan (CN)

(72) Inventors: Yijun Li, Chengdu (CN); Junxuan He, Chengdu (CN); Zhi Jiang, Chengdu (CN); Xiaolin Hu, Chengdu (CN); Leqing Zhang, Chengdu (CN); Deming Wang, Chengdu (CN)

(73) Assignee: Revotek Co., Ltd, Sichuan (CN)

( * ) Notice: Subject to any disclaimer, the term of this patent is extended or adjusted under 35 U.S.C. 154(b) by 484 days.

(21) Appl. No.: 16/252,253

(22) Filed: Jan. 18, 2019

(65) Prior Publication Data

US 2019/0216591 A1    Jul. 18, 2019

(30) Foreign Application Priority Data

Jan. 18, 2018  (CN) .......................... 20181048700.6
Jan. 11, 2019  (CN) .......................... 20191025832.1

(51) Int. Cl.
*A61F 2/06* (2013.01)
*A61L 27/38* (2006.01)
(Continued)

(52) U.S. Cl.
CPC .............. *A61F 2/062* (2013.01); *A61F 2/042* (2013.01); *A61L 27/3808* (2013.01);
(Continued)

(58) Field of Classification Search
CPC ... B29C 64/295; B29C 64/245; B29C 64/209; B29C 64/124; B29L 2031/753;
(Continued)

(56) References Cited

U.S. PATENT DOCUMENTS

2003/0211130 A1* 11/2003 Sanders .................. A61L 27/34
                                                              424/423
2010/0330144 A1* 12/2010 Liu ...................... B05B 13/0442
                                                              424/423
(Continued)

FOREIGN PATENT DOCUMENTS

| CN | 205364554     | 7/2016  |
|----|---------------|---------|
| WO | WO 2016/154882 A1 | 10/2016 |
| WO | WO 2016/201577 A1 | 12/2016 |

OTHER PUBLICATIONS

EP 19152563.3, Jun. 27, 2019, Extended European Search Report.

*Primary Examiner* — Christine H Matthews
*Assistant Examiner* — Joshua Daryl D Lannu
(74) *Attorney, Agent, or Firm* — Wolf, Greenfield & Sacks, P.C.

(57) ABSTRACT

The present disclosure relates to a device for printing a lumen tissue construct, a method for using the same, and a 3D bioprinter. The device includes a spray head assembly for printing a biological construct; and a bioprinting platform for supporting a lumen tissue, and for carrying a biological construct printed by the spray head assembly, and for applying the biological construct to an inner surface of the lumen tissue. The device for printing a lumen tissue construct of the present disclosure provides the spray head assembly and the bioprinting platform, and the spray head assembly applies the biological construct onto the inner surface of the lumen tissue by the bioprinting platform, to avoid such problems as recurrence of thrombus and restenosis of a lumen after the lumen tissue has been implanted for a long time, thereby improving the biological reliability of the lumen tissue.

22 Claims, 11 Drawing Sheets

(51) Int. Cl.
    *A61L 27/50*     (2006.01)
    *A61F 2/04*      (2013.01)
    *B33Y 30/00*     (2015.01)
    *B29C 64/209*    (2017.01)
    *B33Y 10/00*     (2015.01)
    *B29C 64/124*    (2017.01)
    *B29C 64/245*    (2017.01)

(52) U.S. Cl.
    CPC .......... *A61L 27/507* (2013.01); *B29C 64/124* (2017.08); *B29C 64/209* (2017.08); *B33Y 10/00* (2014.12); *B33Y 30/00* (2014.12); *A61F 2/06* (2013.01); *A61F 2240/002* (2013.01); *A61L 27/3834* (2013.01); *B29C 64/245* (2017.08)

(58) Field of Classification Search
    CPC ......... A61F 2/06; A61F 2/2415; B33Y 80/00; B33Y 30/00; B33Y 10/00; A61L 27/507
    See application file for complete search history.

(56) References Cited

U.S. PATENT DOCUMENTS

2018/0112167 A1* 4/2018 Kang .................... B29C 64/321
2020/0086564 A1* 3/2020 Lewis .................... B33Y 40/00

* cited by examiner

DEVICE FOR PRINTING LUMEN TISSUE CONSTRUCT, METHOD FOR USING THE SAME AND 3D BIOPRINTER

CROSS REFERENCE TO RELATED APPLICATION

The present application claims priority from Chinese application number CN201810048700.6 filed Jan. 18, 2018, and Chinese application number CN201910025832.1 filed Jan. 11, 2019, which are herein incorporated by reference.

TECHNICAL FIELD

The present disclosure relates to the technical field of 3D bioprinting, and especially relates to a device for printing lumen tissue construct, a method for using the same and a 3D bioprinter.

BACKGROUND

In the relevant art, common artificial blood vessels are made from polymer fibers (e.g., nylon, dacron), silk, or ePTFE. In the case of vascular implantation, intact artificial blood vessels may be used to replace lesioned or damaged blood vessels. Although the replacement of lesioned or damaged blood vessels with such artificial blood vessels has achieved great clinical results, it is still confronted with difficult problems, including recurrence of thrombus and appearance of restenosis of a lumen after implantation for a long time. The radical cause resulting in these problems lies in the lack of a complete endothelial cell layer on the inner surface of such artificial blood vessels.

In addition, since the artificial blood vessels can hardly be deformed in a radial direction, the relevant art cannot externally compress the artificial blood vessels so that the biological construct formed by bio-ink cannot be completely evenly, intactly, and flatly attached onto the inner wall of the artificial blood vessels.

SUMMARY

A device for printing lumen tissue construct in accordance with some embodiments, includes:

a spray head assembly for printing a biological construct; and a bioprinting platform for supporting a lumen tissue, and for carrying a biological construct printed by the spray head assembly 1, and for applying the biological construct to an inner surface of the lumen tissue.

In some embodiments, the spray head assembly includes:

a bio-ink container for containing bio-ink;

a medical adhesive container for containing medical adhesive; and a nozzle configured to alternatively communicate with the bio-ink container and the medical adhesive container.

In some embodiments, the spray head assembly includes:

a medical adhesive spray head for applying medical adhesive to a surface of the biological construct; and a bio-ink spray head for providing bio-ink to the bioprinting platform so as to print the biological construct.

In some embodiments, the medical adhesive spray head includes:

a medical adhesive container for containing medical adhesive; and a medical adhesive nozzle in communication with the medical adhesive container, for applying the medical adhesive contained in the medical adhesive container to the surface of the biological construct.

In some embodiments, the medical adhesive container and the medical adhesive nozzle are separate or integrated.

In some embodiments, the medical adhesive spray head includes a medical adhesive piston disposed in the medical adhesive container, wherein the medical adhesive piston is adapted to eject the medical adhesive contained in the medical adhesive container.

In some embodiments, the medical adhesive spray head includes a pipette.

In some embodiments, the lumen tissue construct printing device includes a first force applying member for ejecting the medical adhesive from the medical adhesive spray head.

In some embodiments, the first force applying member includes a first air pump for providing an air pressure so as to eject t the medical adhesive from the medical adhesive spray head.

In some embodiments, the first force applying member includes a first plunger pump for providing a thrust so as to eject medical adhesive from the medical adhesive spray head.

In some embodiments, the bio-ink spray head includes:

a bio-ink container for containing bio-ink; and a bio-ink nozzle in communication with the bio-ink container, for ejecting bio-ink contained in the bio-ink container so as to print the biological construct.

In some embodiments, the bio-ink container and the bio-ink nozzle are separate or integrated.

In some embodiments, the bio-ink spray head includes a bio-ink piston disposed in the bio-ink container, wherein the bio-ink piston is adapted to eject the bio-ink within the bio-ink container.

In some embodiments, the bio-ink spray head includes a pipette.

In some embodiments, the lumen tissue construct printing device includes a second force applying member for ejecting the bio-ink from the bio-ink spray head.

In some embodiments, the second force applying member includes a second plunger pump for providing a thrust to eject the bio-ink from the bio-ink spray head.

In some embodiments, the second force applying member includes a second air pump for providing an air pressure so as to eject the bio-ink from the bio-ink spray head.

In some embodiments, the lumen tissue construct printing device includes a third force applying member in communication with the bio-ink container and the bio-ink nozzle, for causing bio-ink contained in the bio-ink container to flow to the bio-ink nozzle.

In some embodiments, the third force applying member includes:

a housing in communication with the bio-ink container and the bio-ink nozzle;

a spiral stator fixedly disposed at an inner wall of the housing; and a spiral rotor rotatably disposed within the housing;

wherein the spiral rotor is configured to cooperate with the spiral stator to supply bio-ink within the housing to the bio-ink nozzle.

In some embodiments, the bioprinting platform includes:

a platform base;

a butt-jointed part, including a hollow rod disposed at the platform base, wherein the hollow rod is adapted to carry the lumen tissue; and a rotary part, including a rotary rod rotatably disposed at the platform base for carrying the biological construct printed by biological ink provided by the spray head assembly; wherein the rotary rod is configured to be insertable into the hollow rod, so as to apply the biological construct carried thereon to the inner surface of the lumen tissue.

In some embodiments, an outer surface of the rotary rod is covered with an elastic film.

In some embodiments, the rotary rod is hollow, and a vent communicating with the inside of the rotary rod is provided on an outer wall of the rotary rod to exhaust air inside the rotary rod to expand the elastic film.

In some embodiments, the lumen tissue construct printing device includes a temperature regulating assembly for regulating a temperature of the biological construct on the rotary rod.

In some embodiments, the temperature regulating assembly includes a heating member disposed inside the rotary rod.

In some embodiments, the temperature regulating assembly includes:

a circulation line, within which there circulatingly flows a refrigerant for adjusting the temperature of the biological construct on the rotary rod; and a pump, disposed on the circulation line, for providing power to cause refrigerant to flow within the circulation line.

In some embodiments, an outer wall of the hollow rod is configured to carry the lumen tissue.

In some embodiments, the lumen tissue construct printing device includes a retaining member, which is adapted to act on a tail end of the lumen tissue so that the lumen tissue is disengaged from the hollow rod, and retained at a periphery of the biological construct on the rotary rod, during a process of disengaging the hollow rod from the rotary rod.

In some embodiments, the lumen tissue construct printing device includes a retaining ring movably disposed at the hollow rod, wherein the retaining ring is located at the tail end of the lumen tissue, and the retaining ring is adapted to cooperate with the retaining member to retain the lumen tissue at a periphery of the biological construct on the rotary rod.

In some embodiments, the bioprinting platform further includes a gripping mechanism for gripping the lumen tissue to support and locate the lumen tissue, so as to attach the lumen tissue to the biological construct.

In some embodiments, the gripping mechanism includes a first gripping block and a second gripping block which are movable with respect to each other.

In some embodiments, the gripping mechanism further includes a limiting block disposed at the bottoms of the first gripping block and the second gripping block, for limiting relative movement of the first gripping block and the second gripping block, so that the first gripping block and the second gripping block are tangent to an outer wall of the lumen tissue.

In some embodiments, the gripping mechanism further includes a support platform disposed at the bottoms of the first gripping block and the second gripping block to support the lumen tissue.

In some embodiments, an outer wall of the rotary rod is covered with an elastic film, the rotary rod is hollow, and a vent communicating with the inside of the rotary rod is provided on the outer wall of the rotary rod to exhaust air inside the rotary rod to expand the elastic film;

The device further includes a baffle located at an end of the rotary rod adjacent to the hollow rod, for avoiding expansion of the elastic film along an axial direction of the rotary rod.

In some embodiments, the hollow rod is configured to carry the lumen tissue therein; the rotary rod is configured to be insertable into the hollow rod, and located within the lumen tissue, so as to apply the biological construct carried thereon to the inner surface of the lumen tissue.

In some embodiments, a first plug is provided at an end of the hollow rod adjacent to the rotary rod, wherein the first plug is provided with a through hole for allowing passage of the rotary rod; a second plug is provided at other end of the hollow rod far away from the rotary rod.

In some embodiments, the second plug is provided with a positioning pin, wherein an annular cavity between the positioning pin and the hollow rod is adapted to position the lumen tissue.

In some embodiments, a gripping slit is provided at an end of the hollow rod adjacent to the rotary rod, so as to facilitate gripping the lumen tissue within the hollow rod by a gripping tool through the gripping slit.

In some embodiments, the butt-jointed part includes a displacement mechanism for driving the hollow rod to move relative to the rotary rod.

In some embodiments, the lumen tissue construct printing device further includes an optical probe for detecting the flatness of an inner wall of the biological construct.

A 3D bioprinter in accordance with some embodiments, includes the device in any one of the above-described embodiments.

A method of printing the lumen tissue construct using the above-described device in accordance with some embodiments, includes a step of covering a layer of elastic film on the outer wall of the rotary rod before printing the biological construct.

In some embodiments, the method further includes a film ballooning step: aerating into the elastic film to balloon the elastic film so that the biological construct is attached to an inner wall of the lumen tissue, after the lumen tissue is sleeved outside the biological construct.

A device for printing lumen tissue constructin accordance with some embodiments, includes a spray head assembly and a bioprinting platform, wherein the spray head assembly prints a biological construct on an inner surface of a lumen tissue by the bioprinting platform.

Further, the spray head assembly includes a medical adhesive spray head, the medical adhesive spray head including a medical adhesive container and a medical adhesive nozzle, wherein a top of the medical adhesive container is connected with an air pump, through an air path in which a vacuum generator is provided for generating a negative pressure for the medical adhesive container in a non-printing state.

Further, the spray head assembly includes a bio-ink spray head that includes a screw pump and a bio-ink nozzle.

Further, the screw pump includes a spiral stator and a spiral rotor for extruding bio-ink within the screw pump to the bio-ink nozzle, wherein the spiral stator is made of a silicone material.

Further, a printing outlet end of the bio-ink nozzle has a chamfer, which has a chamfered surface defining an included angle of 10° to 30° with a center line of a printing outlet of the bio-ink nozzle.

Further, the included angle is 20°.

Further, an outer surface at the printing outlet end of the bio-ink nozzle has a roughness Ra≤0.4.

Further, the bioprinting platform includes a platform base, a rotary part and a butt-jointed part movable relative to the rotary part, wherein the rotary part includes a rotary rod for carrying the bio-ink and the medical adhesive to form a biological construct, and the butt-jointed part includes a hollow rod having an outer wall for carrying the lumen tissue.

Further, the outer wall of the rotary rod is covered with an elastic film.

Further, an interior of the rotary rod is hollow, and the outer wall of the rotary rod is provided with a vent communicating with the interior, for exhausting air inside the rotary rod to expand the elastic film.

Further, the interior of the rotary rod is further provided with a heating member.

Further, the heating member includes a heating section and a spacing section that are spacedly arranged, wherein the heating section has a surface wound with a resistance wire, and the heating section has a diameter that is less than that of the spacing section.

Further, a temperature detecting member is provided at an end of the heating member adjacent to the butt-jointed part, for detecting the temperature of the heating member.

Further, the bioprinting platform further includes a gripping mechanism for gripping the lumen tissue to make it disengaged from the hollow rod and socketed to the biological construct.

Further, the gripping mechanism includes a first gripping block and a second gripping block which are movable with respect to each other.

Further, the gripping mechanism further includes a retaining member for acting on a tail end of the lumen tissue so that it is disengaged from the hollow rod.

Further, the retaining member is cooperatively provided with a retaining ring acting on the tail end of the lumen tissue.

Further, the gripping mechanism further includes a limiting block provided at the bottoms of the first gripping block and the second gripping block, for limiting relative movement of the first gripping block and the second gripping block, so that the first gripping block and the second gripping block are both tangent to the outer wall of the lumen tissue.

Further, the gripping mechanism further includes a support platform provided at the bottoms of the first gripping block and the second gripping block to support the lumen tissue.

Further, the device also includes an optical probe movable inside the rotary rod, for detecting a flatness of the inner wall of the biological construct, wherein the rotary rod is made of a transparent material.

Further, the optical probe is movably disposed within the rotary rod or the hollow rod.

Further, the optical probe is fixedly disposed within the hollow rod.

Further, the device includes a reservoir provided below the rotary rod, for carrying a bioprinting construct disengaged and falling from the gripping mechanism.

A 3D bioprinter in accordance with some embodiments, which includes the aforementioned device for printing lumen tissue construct.

A method of printing lumen tissue construct using the aforementioned device, which includes a step of covering a layer of elastic film on the outer wall of the rotary rod before printing the biological construct.

Further, there also includes a ballooning step: aerating into the elastic film to balloon the elastic film so that the biological construct is attached to the inner wall of the lumen tissue, after the lumen tissue is sleeved outside the biological construct.

Therefore, based on the aforementioned technical solution, the device for printing lumen tissue construct of the present disclosure provides the spray head assembly and the bioprinting platform, and the spray head assembly prints the biological construct on the inner surface of the lumen tissue by the bioprinting platform, to avoid such problems as recurrence of thrombus and restenosis of a lumen after the lumen tissue has been implanted for a long time, thereby improving the biological reliability of the lumen tissue. The method of printing lumen tissue construct and the 3D bioprinter provided by the present disclosure also correspondingly have the advantageous technical effects described above.

BRIEF DESCRIPTION OF THE DRAWINGS

The drawings described herein are used to provide a further understanding of the present disclosure and constitute a part of the present application. The illustrative embodiments of the present disclosure as well as the descriptions thereof, which are merely adapted to explain the present disclosure, do not constitute improper definitions on the present disclosure. In the drawings.

Various reference signs respectively represent:

1—spray head assembly;

11—medical adhesive spray head; 111—medical adhesive container; 112—medical adhesive nozzle; 113—medical adhesive piston;

12—bio—ink spray head; 121—screw pump; 1211—spiral stator; 1212—spiral rotor; 1213—inlet connecting piece; 122—bio—ink nozzle; 123—thermal insulation shell; 124—bio—ink piston; 125—bio—ink container; 126—semiconductor cooling plate; 127—connecting tube; 128—bio—ink inlet; 129—thermal insulation sleeve;

13—injection member; 131—injector; 132—sliding block; 133—fixing plate;

14—pipette;

2—bioprinting platform;

21—rotary part; 211—rotary rod; 212—heating member; 2121—heating section; 2122—connecting groove; 2123—spacing section; 213—temperature detecting member; 214—sealing ring; 215—circulation line;

22—gripping mechanism; 221, 221'—first gripping block; 222, 222'—second gripping block; 223, 223'—retaining member; 224—support platform; 225—limiting block; 226—baffle;

23—butt—jointed part; 231—hollow rod; 232—displacement mechanism; 233—first plug; 234—second plug; 235—gripping slit; 236—mechanical arm; 237—retaining ring.

DETAILED DESCRIPTION

Next, the technical solution of the present disclosure is further described in detail by means of the drawings and embodiments.

The specific embodiments of the present disclosure are further described in order to facilitate understanding of the concept of the present disclosure, the technical problem to be solved, the technical features constituting the technical solution and the technical effect produced therefrom. It is necessary to explain that, the explanations for such embodiments do not constitute definitions on the present disclosure. In addition, the technical features involved in the embodiments of the present disclosure described below may be combined with each other as long as they do not constitute a conflict therebetween.

The technical problem solved by the present disclosure is to provide a device for printing lumen tissue construct, a method for using the same and a 3D bioprinter, aiming at improving the biological reliability of the lumen tissue.

Figure 1:
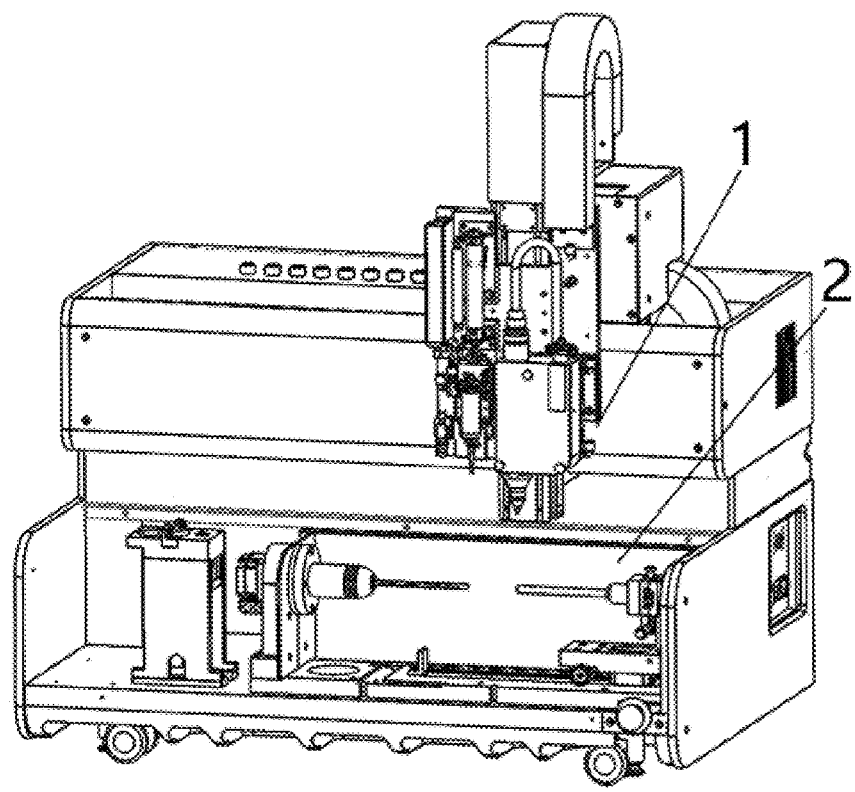
FIG. 1 is a schematic view of an overall structure of the device for printing lumen tissue construct provided by some embodiments of the present disclosure.

In some illustrative embodiments of the device for printing lumen tissue construct of the present disclosure, as shown in FIG. 1, the device includes a spray head assembly 1 and a bioprinting platform 2, in which the spray head assembly 1 prints a biological construct on an inner surface of a lumen tissue by the bioprinting platform 2.

In some embodiments, the lumen tissue includes a body duct such as a blood vessel, a trachea, an esophagus, an intestinal canal, a urinary catheter, or the like.

Among them, the lumen tissue is especially an artificial blood vessel, such as a commercial blood vessel of Gore, and the occurrence of thrombus after an artificial blood vessel has been implanted for a long time may be avoided by printing the biological construct on the inner surface of the artificial blood vessel.

In some illustrative embodiments, in which a spray head assembly 1 and a bioprinting platform 2 are provided, the spray head assembly 1 prints the biological construct on the inner surface of the lumen tissue by the bioprinting platform 2, to avoid such problems as recurrence of thrombus and restenosis of a lumen after the lumen tissue (specifically a blood vessel) has been implanted for a long time, thereby improving the biological reliability of the lumen tissue.

The device for printing lumen tissue construct provided by the present disclosure is adapted to effectuate printing a multi-specification biological construct applied to the lumen tissue.

In some embodiments, as shown in FIG. 1, the device for printing lumen tissue construct includes a spray head assembly 1 for printing a biological construct.

In some embodiments, the device for printing lumen tissue construct includes a bioprinting platform 2 for supporting the lumen tissue, and for carrying the biological construct printed by the spray head assembly 1, and for applying the biological construct to the inner surface of the lumen tissue to form a lumen tissue construct.

In some embodiments, the spray head assembly 1 includes a bio-ink container 125 for containing bio-ink which is adapted to print a biological construct on the bioprinting platform 2.

In some embodiments, the spray head assembly 1 includes a medical adhesive container 111 for containing medical adhesive. Medical adhesive is applied to the biological construct, so as to apply the biological construct to the inner surface of the lumen tissue.

In some embodiments, the spray head assembly 1 includes a nozzle configured to alternatively communicate with the bio-ink container 125 and the medical adhesive container 111.

In some embodiments, the same nozzle is adapted to respectively print the biological construct and apply the medical adhesive. For example, the same pipette or syringe and the like is adapted to print the bio-ink before printing the medical adhesive.

In some embodiments, the nozzle includes a syringe-type structure, for example, the medical adhesive or bio-ink is ejected by a piston to perform printing. This manner can avoid residual medical adhesive or bio-ink, and solve wall sticking (liquid hanging in the internal surface of the container) problem of the medical adhesive and the bio-ink.

In some embodiments, the nozzle includes a pipette that may be used to directly withdraw the medical adhesive or bio-ink from the adhesive cartridge or ink cartridge, so as to perform printing.

Figure 2:
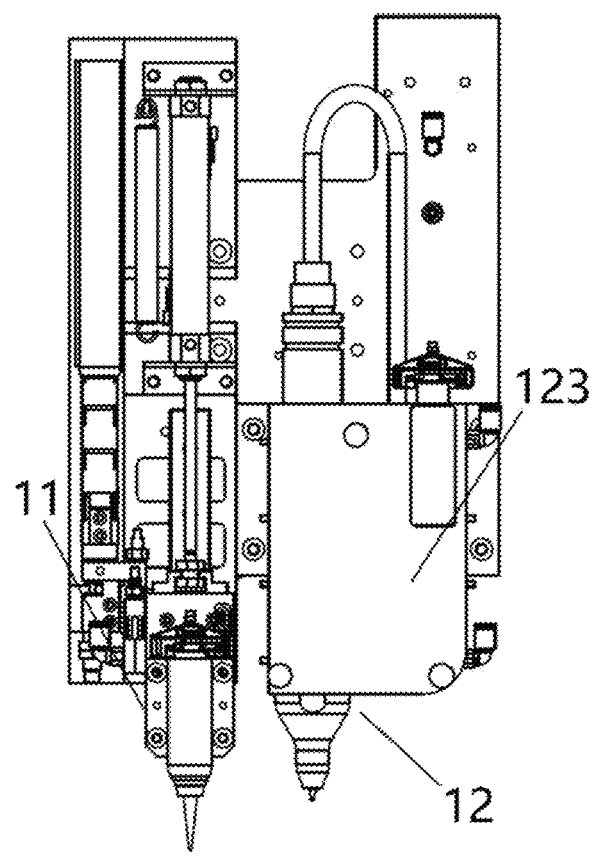
FIG. 2 is a schematic view of an overall structure of a spray head assembly in the device for printing lumen tissue construct provided by some embodiments of the present disclosure.

In some embodiments, as shown in FIG. 2, the spray head assembly 1 includes a medical adhesive spray head 11 for applying medical adhesive to a surface of the biological construct.

In some embodiments, the spray head assembly 1 includes a bio-ink spray head 12 for providing bio-ink to the bioprinting platform 2 so as to print the biological construct.

In some embodiments, the bio-ink and the medical adhesive are provided using different spray heads respectively.

In some embodiments, the medical adhesive spray head 11 includes a medical adhesive container 111 for containing medical adhesive.

In some embodiments, the medical adhesive spray head 11 includes a medical adhesive nozzle 112 in communication with the medical adhesive container 111, for applying the medical adhesive contained in the medical adhesive container 111 to the surface of the biological construct.

In some embodiments, the medical adhesive container 111 and the medical adhesive nozzle 112 are separate or integrated.

In some embodiments, the medical adhesive spray head 11 includes a pipette, inside which it is possible to store medical adhesive and achieve printing. The pipette may directly withdraw the medical adhesive from the adhesive cartridge and apply the medical adhesive on the surface of the biological construct.

In some embodiments, the medical adhesive spray head 11 includes a medical adhesive piston 113. The medical adhesive piston 113 is disposed in the medical adhesive container 111 for ejecting the medical adhesive contained in the medical adhesive container 111, so as to avoid residual medical adhesive on the inner wall of the medical adhesive container 111, and solve the wall sticking problem of the medical adhesive.

Figure 3:
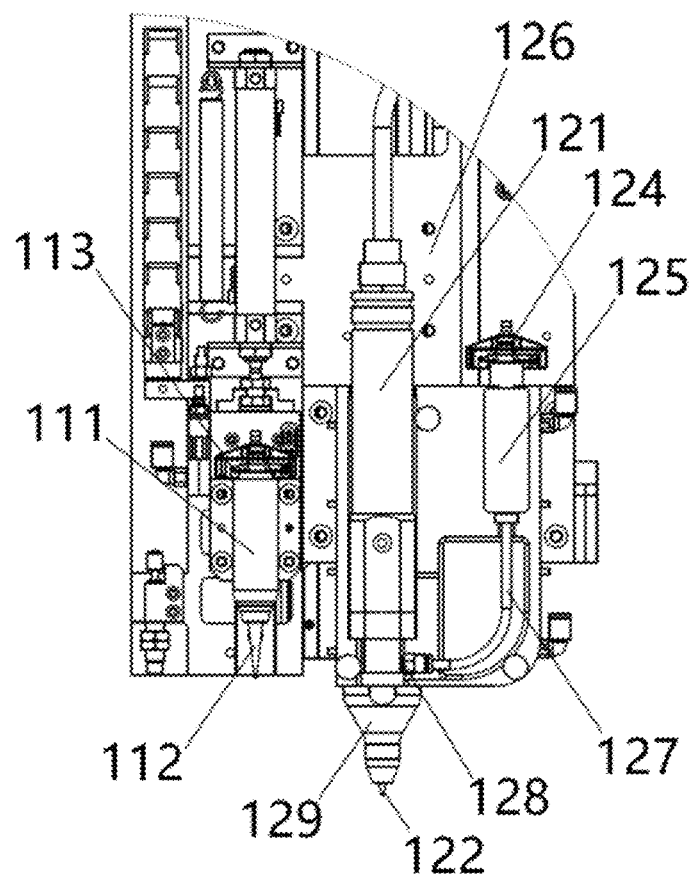
FIG. 3 is a schematic view of an interior structure of a spray head assembly in the device for printing lumen tissue construct provided by some embodiments of the present disclosure.

Alternatively, as shown in FIG. 3, the medical adhesive spray head 11 includes a syringe-type structure.

The medical adhesive piston 113 of a syringe-type structure is powered by the first force applying member to move so as to eject the medical adhesive contained in the medical adhesive container 111.

In some embodiments, the device for printing lumen tissue construct includes a first force applying member for ejecting the medical adhesive from the medical adhesive spray head 11.

In some embodiments, the first force applying member includes a first air pump for providing an air pressure so as to eject the medical adhesive from the medical adhesive spray head 11.

In some embodiments, the device for printing lumen tissue construct includes a vacuum generator disposed between the air pump and the medical adhesive spray head 11, for generating a negative pressure that is counteracted by the gravity of the medical adhesive in a non-printing state.

In some embodiments, the first force applying member includes a first plunger pump for providing a thrust so as to eject the medical adhesive from the medical adhesive spray head 11.

Alternatively, the plunger in the first plunger pump is the same member as the medical adhesive piston 113, or is a different member. Relative to the manner of ejecting the medical adhesive by an air pressure, the manner of ejecting the medical adhesive using a piston may effectuate accurate control in application of the medical adhesive, without fluctuation in accuracy resulting from air compression or expansion and the like.

In some embodiments, the first plunger pump includes a gear, a rack and a plunger. The gear drives the rack to move up and down. The plunger is disposed at a lower end of the rack which moves up and down to drive the plunger to move up and down, so as to change an air pressure within the medical adhesive container 111, and effectuate suction and spraying of the medical adhesive.

Of course, the first force applying member is not limited to an air pump and a plunger pump.

In some embodiments, the bio-ink spraying head 12 includes a bio-ink container 125 for containing bio-ink.

In some embodiments, the bio-ink spray head 12 includes a bio-ink nozzle 122 in communication with the bio-ink container 125, for ejecting bio-ink contained in the bio-ink container 125 so as to print the biological construct.

In some embodiments, the bio-ink container 125 and the bio-ink nozzle 122 are separate or integrated.

In some embodiments, the bio-ink spraying head 12 includes a bio-ink piston 124 disposed in the bio-ink container 125 for ejecting bio-ink contained in the bio-ink container 125, so as to avoid residual bio-ink on the inner wall of the bio-ink container 125, which causes waste of bio-ink, and solve the wall sticking problem of bio-ink.

Figure 17:
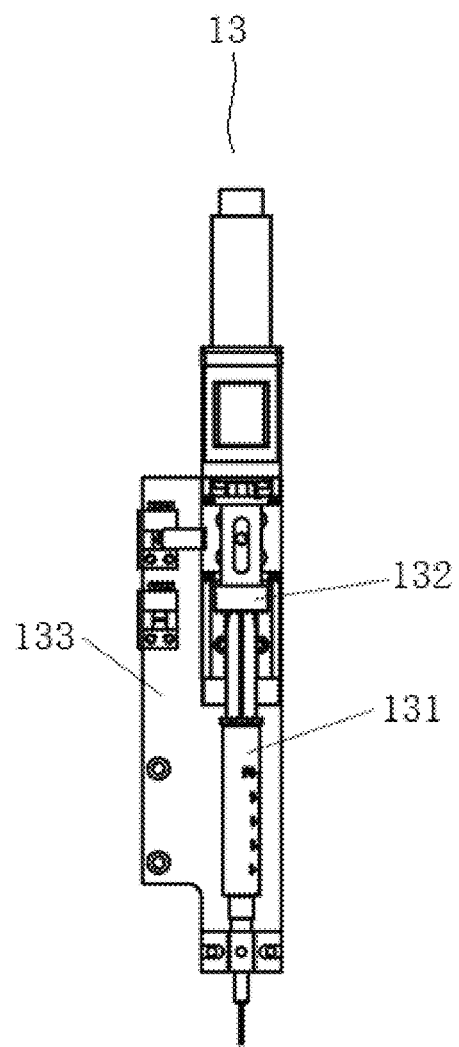
FIG. 17 is a schematic view of the structure of an injection member in the device for printing lumen tissue construct provided by some embodiments of the present disclosure.

Alternatively, as shown in FIG. 17, the bio-ink spraying head 12 includes a syringe-type structure.

Figure 18:
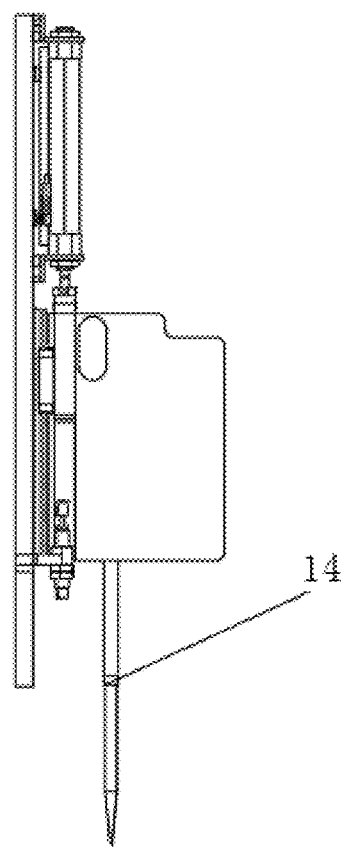
FIG. 18 is a schematic view of the structure of a pipette in the device for printing lumen tissue construct provided by some embodiments of the present disclosure.

In some embodiments, as shown in FIG. 18, the bio-ink spraying head 12 includes a pipette 14. It is possible to store bio-ink and achieve printing inside the pipette 14. The syringe 14 may directly withdraw bio-ink from the ink cartridge and print the bio-ink to create a biological construct.

In some embodiments, the device for printing lumen tissue construct includes a second force applying member for injecting the bio-ink from the bio-ink spray head 12.

In some embodiments, the second force applying member includes a second plunger pump for providing a thrust to eject the bio-ink from the bio-ink spray head 12. It is possible to accurately spray dosed bio-ink using the second plunger pump.

Alternatively, the plunger in the second plunger pump may be the same member as the bio-ink piston 124, or may also be a different member. Relative to the manner of ejecting the bio-ink by an air pressure, the manner of ejecting the bio-ink using a piston may effectuate accurate control in application of the bio-ink, without fluctuation in accuracy resulting from air compression or expansion and the like.

In some embodiments, the second plunger pump includes a gear, a rack and a plunger. The gear drives the rack to move up and down. The plunger is disposed at a lower end of the rack which moves up and down, so as to change an air pressure within the bio-ink container 125, and effectuate suction and spraying.

In some embodiments, the second force applying member includes a second air pump which provides an air pressure so as to eject the bio-ink from the bio-ink spray head 12.

Of course, the second force applying member is not limited to a plunger pump and an air pump.

In some embodiments, as shown in FIG. 17, the bio-ink spraying head 12 includes an injection member 13. The injection member 13 includes a syringe 131, a sliding block 132 and a fixing plate 133. The bio-ink piston of the syringe 131 is connected with the sliding block 132, which is movably disposed at the fixing plate 133 and slidable along a chute provided along the fixing plate 133.

In some embodiments, the second force applying member is controlled by the control system to drive the sliding block 132 to move up and down on the fixing plate 133.

In some embodiments, the syringe 131 may be a container for preparing the bio-ink in an earlier period. After the bio-ink is prepared, the syringe 131 is movingly mounted to the fixing plate 133, and the plunger pump provides power to press the bio-ink piston within the syringe 131 downwards, so as to effectuate printing the bio-ink and maintaining a uniform discharge.

In some embodiments, the device for printing lumen tissue construct includes a third force applying member in communication with the bio-ink container 125 and the bio-ink nozzle 122, for causing bio-ink within the bio-ink container 125 to flow to the bio-ink nozzle 122.

Figure 4:
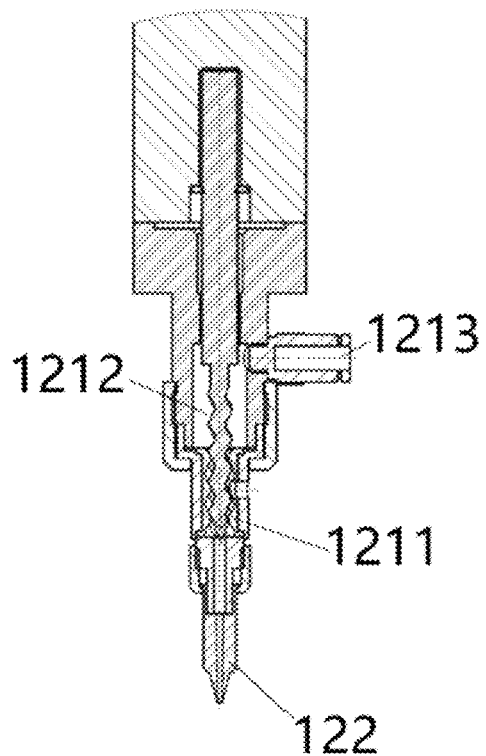
FIG. 4 is a schematic view of a sectional structure of a screw pump in the device for printing lumen tissue construct provided by some embodiments of the present disclosure.

In some embodiments, as shown in FIG. 4, the third force applying member includes a housing in communication with the bio-ink container 125 and the bio-ink nozzle 122.

In some embodiments, the third force applying member includes a spiral stator 1211 fixedly disposed at an inner wall of the housing.

In some embodiments, the third force applying member includes a spiral rotor 1212 rotatably disposed within the housing.

In some embodiments, the spiral rotor 1212 is configured to cooperate with the spiral stator 1211 to supply bio-ink within the housing to the bio-ink nozzle 122.

In some embodiments, the spiral stator 1211 is made from a silicone material.

In some embodiments, the third force applying member includes a screw pump.

Figure 5:
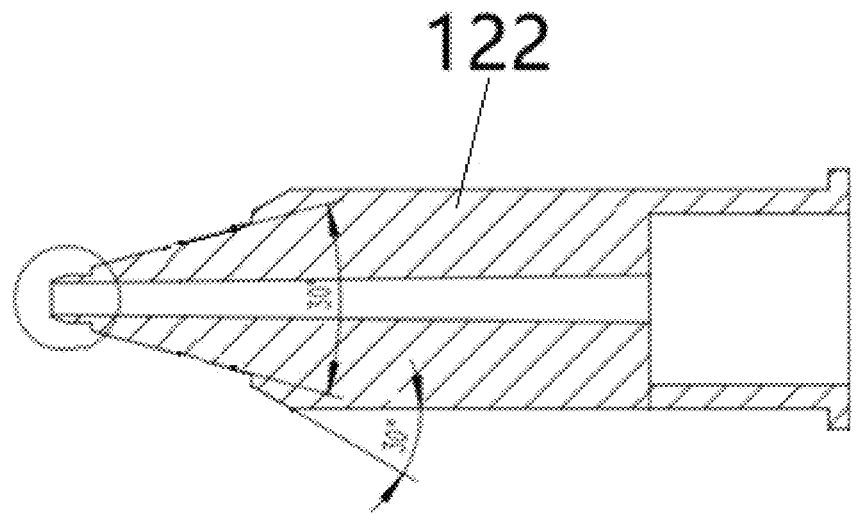
FIG. 5 is a schematic view of a sectional structure of a bio-ink nozzle in the device for printing lumen tissue construct provided by some embodiments of the present disclosure.

In some embodiments, as shown in FIG. 5, a printing outlet end of the bio-ink nozzle 122 has a chamfer, which has a chamfered surface defining an included angle of 10° to 30° with a center line of a printing outlet of the bio-ink nozzle 122.

Figure 6:
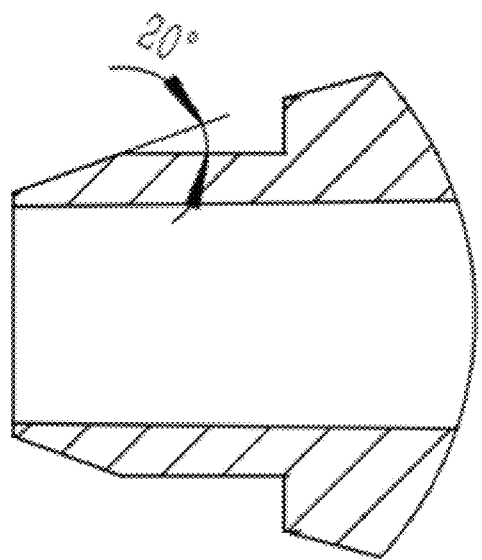
FIG. 6 is a partially enlarged schematic view of a circled portion in FIG. 5.

In some embodiments, as shown in FIG. 6, the included angle is 20°.

In some embodiments, an outer surface at the printing outlet end of the bio-ink nozzle 122 has a roughness Ra≤0.4.

Figure 7:
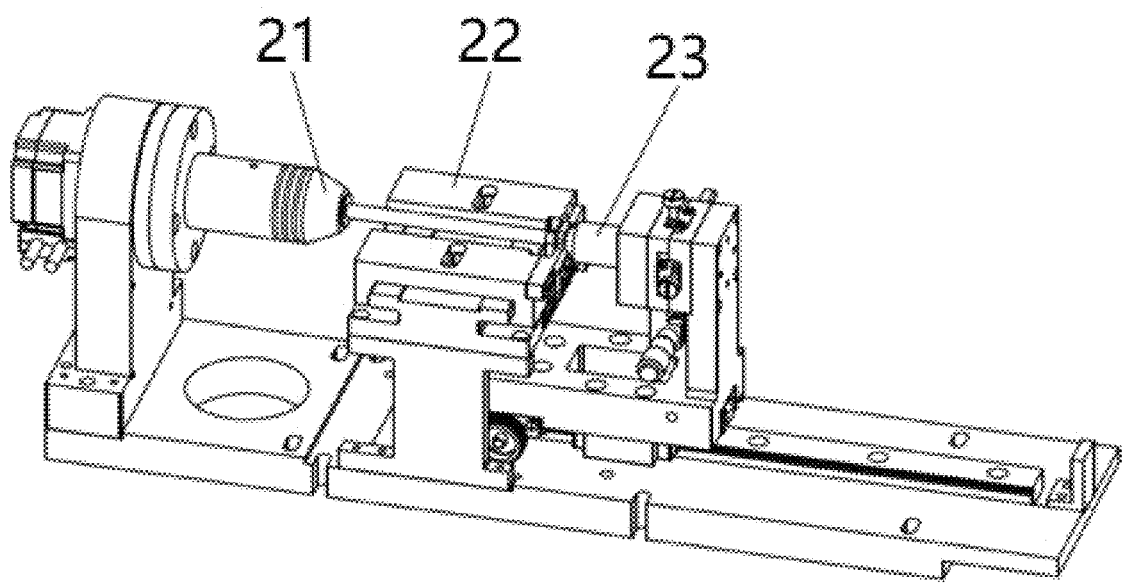
FIG. 7 is a schematic view of an overall structure of a first embodiment of a bioprinting platform in the device for printing lumen tissue construct provided by some embodiments of the present disclosure.

In some embodiments, as shown in FIG. 7, the bioprinting platform 2 includes a platform base.

Figure 8:
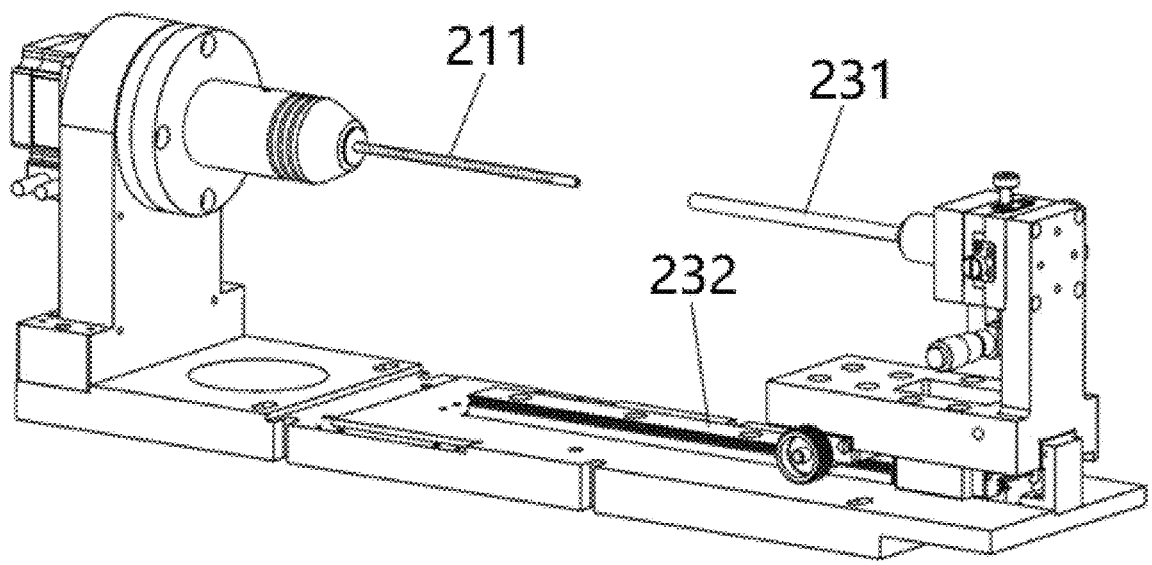
FIG. 8 is a schematic view of a partial structure of a first embodiment of a bioprinting platform in the device for printing lumen tissue construct provided by some embodiments of the present disclosure.

In some embodiments, as shown in FIG. 8, the bioprinting platform 2 includes a butt-jointed part 23, which includes a hollow rod 231 that is disposed at the platform base and used to carry the lumen tissue.

In some embodiments, the bioprinting platform 2 includes a rotary part 21, which includes a rotary rod 211 that is rotatably disposed at the platform base. The rotary rod 211 is adapted to carry the biological construct printed by the bio-ink provided by the spray head assembly 1.

The rotary rod 211 is configured to be insertable into the hollow rod 231, so as to apply the biological construct carried thereon to the inner surface of the lumen tissue.

In some embodiments, the outer surface of the rotary rod 211 is covered with an elastic film.

Figure 9:
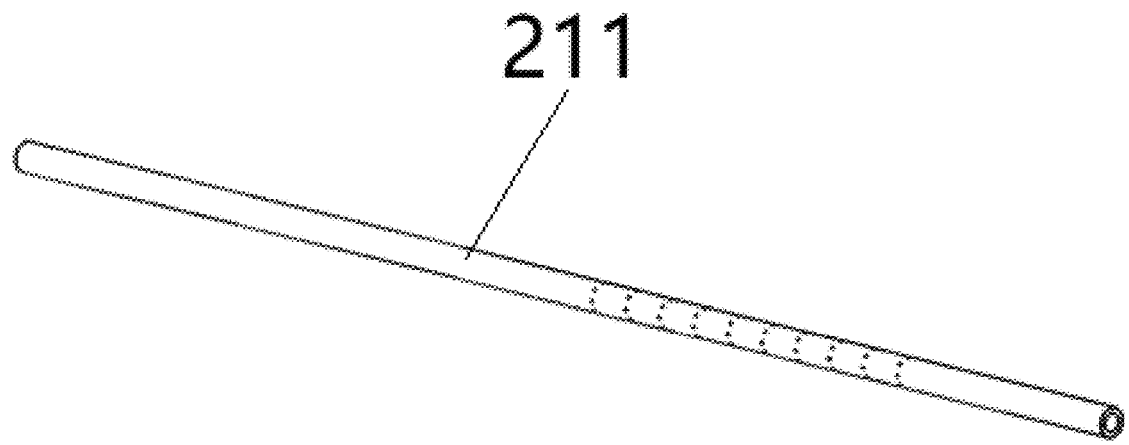
FIG. 9 is a schematic view of the structure of a rotary rod in the device for printing lumen tissue construct provided by some embodiments of the present disclosure.

In some embodiments, as shown in FIG. 9, the rotary rod 211 is hollow, and a vent communicating with the inside of the rotary rod 211 is provided on an outer wall of the rotary rod 211 to exhaust air inside the rotary rod 211 to expand the elastic film.

In some embodiments, the device for printing lumen tissue construct includes a temperature regulating assembly for regulating a temperature of the biological construct on the rotary rod 211, for example reducing a temperature of the biological construct, or increasing a temperature of biological construct.

Figure 10:
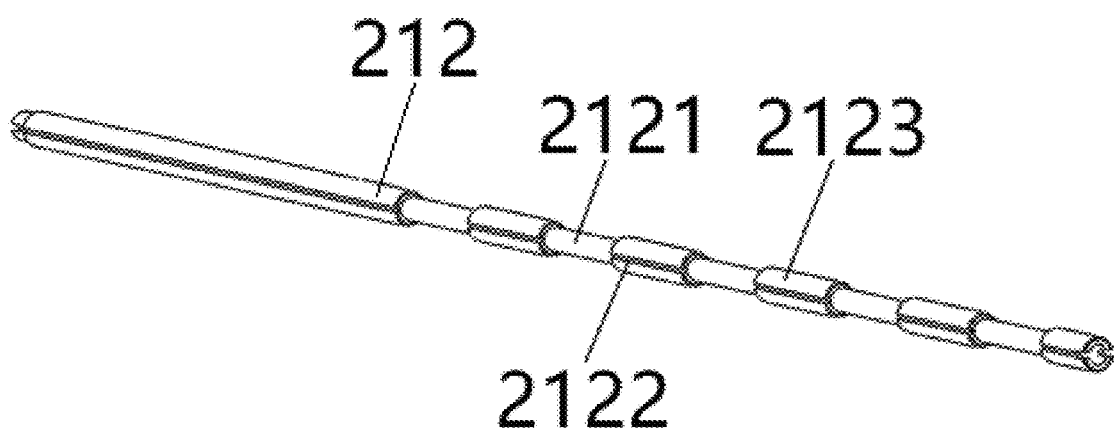
FIG. 10 is a schematic view of the structure of a heating member in the device for printing lumen tissue construct provided by some embodiments of the present disclosure.

In some embodiments, as shown in FIG. 10, the temperature regulating assembly includes a heating member 212 that is disposed inside the rotary rod 211.

In some embodiments, the heating member 212 includes a heating section 2121 and a spacing section 2123 that are spacedly arranged, wherein the heating section 2121 has a surface wound with a resistance wire, and the heating section 2121 has a diameter that is less than that of the spacing section 2123.

Figure 11:
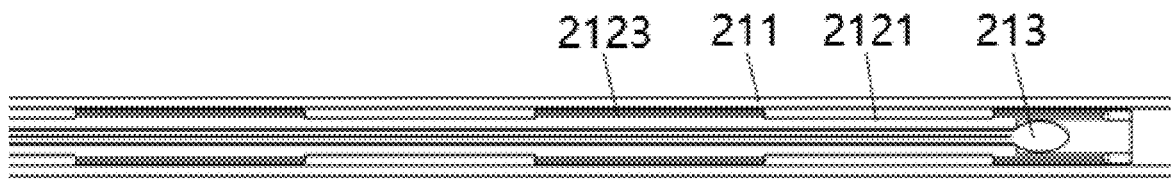
FIG. 11 is a schematic view of the structure of the heating member disposed inside the rotary rod in the device for printing lumen tissue construct provided by some embodiments of the present disclosure.

In some embodiments, as shown in FIG. 11, a temperature detecting member 213 is provided at an end of the heating member 212 adjacent to the butt-jointed part 23, for detecting a temperature of the heating member 212.

In some embodiments, as shown in FIGS. 19-22, the temperature regulating assembly includes a circulation line 215, within which there circulatingly flows a refrigerant for adjusting a temperature of the biological construct on the rotary rod 211.

In some embodiments, the temperature regulating assembly includes a pump, disposed on the circulation line 215, for providing power to cause refrigerant to flow within the circulation line 215.

In some embodiments, an outer wall of the hollow rod 231 is configured to carry the lumen tissue.

In some embodiments, the device for printing lumen tissue construct further includes a retaining member 223, 223', which is adapted to act on a tail end of the lumen tissue so that the lumen tissue is disengaged from the hollow rod 231, and the lumen tissue is retained at a periphery of the biological construct on the rotary rod 211, during a process of disengaging the hollow rod 231 from the rotary rod 211.

The retaining member 223 is adjustable in position. In the movement process of the hollow rod 231 toward the rotary rod 211, the retaining member 223 is far away from the rotary rod 211, so as to avoid that the hollow rod 231 is butt-jointed to the rotary rod 211; in the disengagement process of the hollow rod 231 from the rotary rod 211, the retaining member 223 is adjacent to the rotary rod 211 and acts on the tail end of the lumen tissue.

Figure 19:
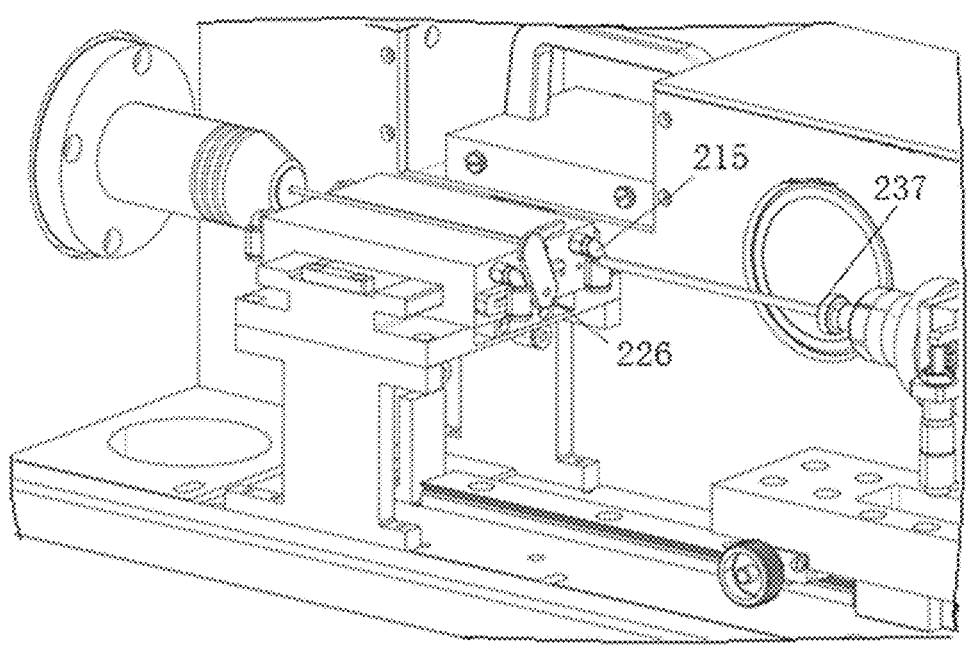
FIG. 19 is a schematic view of the structure of a gripping mechanism in the device for printing lumen tissue construct provided by some embodiments of the present disclosure, in which a baffle is provided.

Since the retaining member 223 acts on the tail end of the lumen tissue, the retaining member 223 is required to have high precision and high degree of cooperation with the lumen tissue. Thus, in some embodiments, as shown in FIG. 19, the device for printing lumen tissue construct includes a retaining ring 237 movably disposed on the hollow rod 231 and located at the tail end of the lumen tissue.

The inner diameter of the retaining ring 237 is slightly larger than the outer diameter of the hollow rod 231, and smaller than the outer diameter of the lumen tissue, so as to facilitate the movement of the retaining ring 237 relative to the hollow rod 231. The outer diameter of the retaining ring 237 is larger than that of the lumen tissue.

In the disengagement process of the hollow rod 231 from the rotary rod 211, the retaining ring 237 is adapted to cooperate with the retaining member 223 to limit a position, such that the retaining member 223 restricts the retaining ring 237 from moving along with the hollow rod 231, and the retaining ring 237 restricts the lumen tissue from moving along with the hollow rod 231. Thus, the lumen tissue may be retained at a periphery of the biological construct on the rotary rod 211.

In some embodiments, the bioprinting platform 2 further includes a gripping mechanism 22 for gripping the lumen tissue to support and locate the lumen tissue, so as to attach the lumen tissue to the biological construct. The gripping mechanism 22 clamps the lumen tissue, so that the lumen tissue is concentric with the biological construct, to prevent that the upper side of the lumen tissue is hung on the rotary rod 211 under the effect of gravity, so that the lower side of the lumen tissue is unsatisfactorily attached to the biological construct.

The gripping mechanism 22 abuts closely against the lumen tissue from the outside, and the elastic film blows up to facilitate attaching the biological construct to the lumen tissue.

In some embodiments, as shown in FIGS. 13-16, the gripping mechanism 22 includes a first gripping block 221, 221' and a second gripping block 222, 222' which are movable with respect to each other. The first gripping block 221, 221' and the second gripping block 222, 222' are approximated to cooperatively support the lumen tissue.

Alternatively, the space for supporting the lumen tissue formed after approximating the first gripping block 221 and the second gripping block 222 is V-shaped. The first gripping block 221 and the second gripping block 222 cooperatively support the lumen tissue, so as to ensure that the lumen tissue is concentric to the biological construct inside the same.

Alternatively, the space for supporting the lumen tissue formed after approximating the first gripping block 221' and the second gripping block 222' is circular. The first gripping block 221' cooperates with the second gripping block 222' to extrude and support the lumen tissue from the outside to the inside, so that the biological construct after being propped up by the elastic film is better attached to the inner wall of the lumen tissue. At the same time, the first gripping block 221' cooperates with the second gripping block 222' also to ensure that the lumen tissue is concentric to the biological construct inside the same to certain extent.

In some embodiments, the retaining members 223, 223' are disposed at the gripping mechanism 22.

In some embodiments, the gripping mechanism 22 further includes a limiting block 225 disposed at the bottoms of the first gripping block 221 and the second gripping block 222, for limiting relative movement of the first gripping block 221 and the second gripping block 222, so that the first gripping block 221 and the second gripping block 222 are tangent to the outer wall of the lumen tissue.

In some embodiments, the gripping mechanism 22 further includes a support platform 224 provided at the bottoms of the first gripping block 221 and the second gripping block 222 to support the lumen tissue, so as to further ensure that the lumen tissue is concentric to the biological construct.

In some embodiments, the outer surface of the rotary rod 211 is covered with an elastic film.

In some embodiments, the rotary rod 211 is hollow, and a vent communicating with the inside of the rotary rod 211 is provided on an outer wall of the rotary rod 211 to exhaust air inside the rotary rod 211 to expand the elastic film.

In some embodiments, the circulation line 215 of the temperature regulating assembly is disposed within the first gripping block 221 and the second gripping block 222. The refrigerant within the circulation line 215 includes warm water or ice water, coolant, and the like. The refrigerant is circulated to flow within the circulation line 215 to achieve temperature control, for example, heating up or cooling down, and the like.

In some embodiments, as shown in FIG. 19, the device for printing lumen tissue construct further includes a baffle 226 located at an end of the rotary rod 211 adjacent to the hollow rod 231, for avoiding expansion of the elastic film along an axial direction of the rotary rod 211.

In some embodiments, the baffle 226 is disposed at an extremity of the gripping mechanism 22. Alternatively, the baffle 226 is a sheet structure.

One end of the baffle 226 is connected to a gripping block by a fixing shaft, such that the baffle 226 is rotatable, and the other end of the baffle 226 is rotatable to one end of the rotary rod 211 proximate to the hollow rod 231, with a small gap from an extremity of the rotary rod 211, for retaining the elastic film and avoiding expansion and popup of the elastic film along an axial direction of the rotary rod 211, upon expansion of the elastic film on the rotary rod 211.

Figure 20:
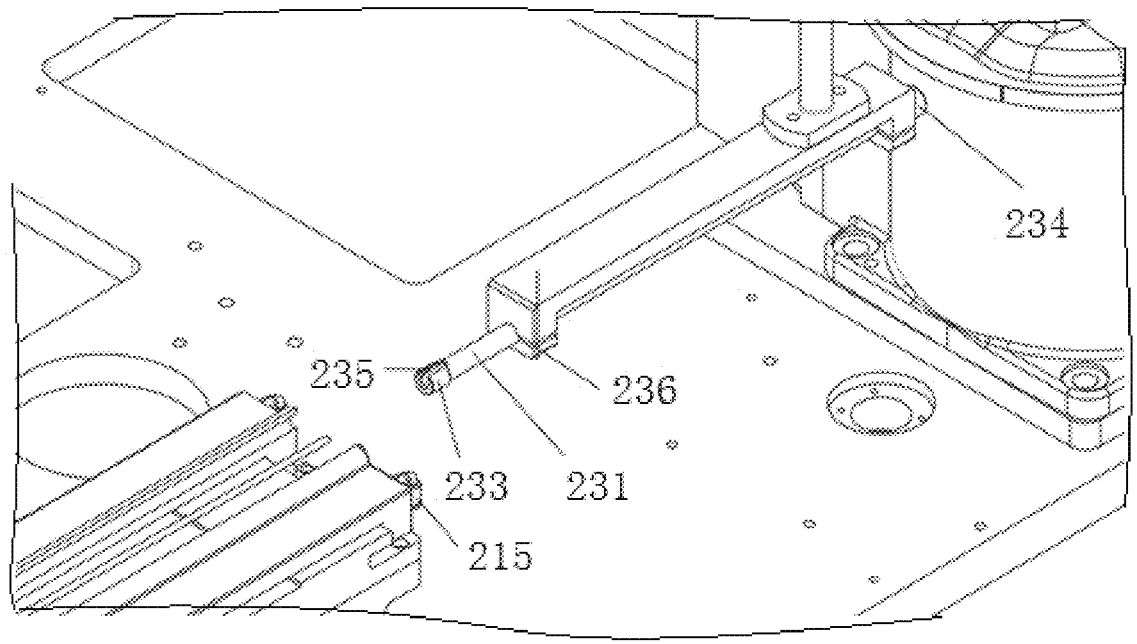
FIG. 20 is a schematic view of a partial structure of a second embodiment of a bioprinting platform in the device for printing lumen tissue construct provided by some embodiments of the present disclosure.
Figure 21:
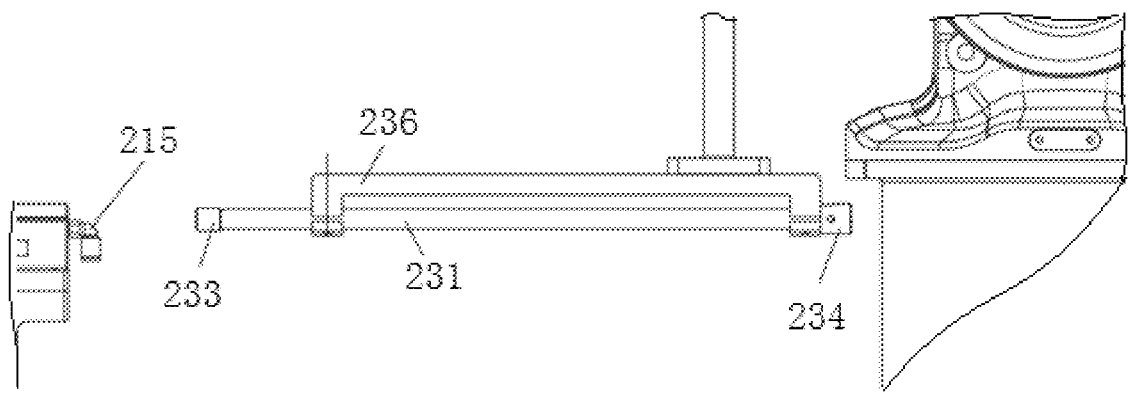
FIG. 21 is a schematic view of the structure of a hollow rod in a second embodiment of a bioprinting platform in the device for printing lumen tissue construct provided by some embodiments of the present disclosure.
Figure 22:
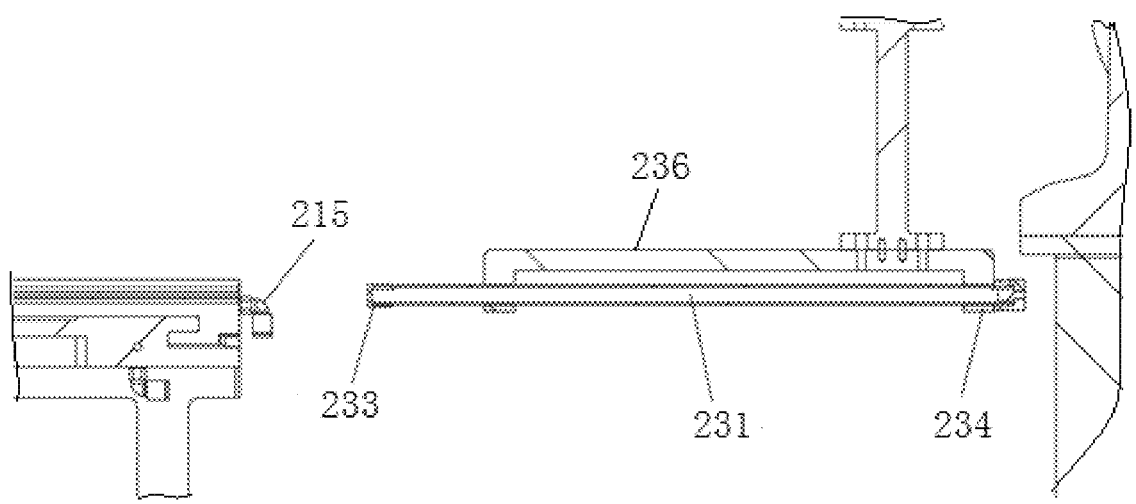
FIG. 22 is a schematic perspective view of the structure of a hollow rod in a second embodiment of a bioprinting platform in the device for printing lumen tissue construct provided by some embodiments of the present disclosure.

In some embodiments, as shown in FIGS. 20-22, the hollow rod 231 is configured to carry the lumen tissue therein; the rotary rod 211 is configured to be insertable into the hollow rod 231, and located within the lumen tissue, so as to apply the biological construct carried thereon to the inner surface of the lumen tissue.

In some embodiments, a first plug 233 is provided at an end of the hollow rod 231 adjacent to an end of the rotary rod 211, wherein the first plug 233 is provided with a through hole for allowing passage of the rotary rod 211.

In some embodiments, a second plug 234 is provided at other end of the hollow rod 231 far away from the rotary rod 211.

In some embodiments, the second plug 234 is provided with a positioning pin, wherein an annular cavity between the positioning pin and the hollow rod 231 is adapted to position the lumen tissue.

In some embodiments, the hollow rod 231 is configured to carry the lumen tissue therein; it is unnecessary to exit from the hollow rod 231 after the lumen tissue is sleeved outside the rotary rod 211.

In order to enable the lumen tissue to be fixed within the hollow rod 231, the inner diameter of the hollow rod 231 is substantially the same as the outer diameter of the lumen tissue, and the first plug 233 and the second plug 234 are respectively disposed in front or rear of the hollow rod 231.

The second plug 234 is a cylindrical structure, with a cylindrical positioning pin provided at an end thereof, wherein an annular space between the positioning pin and the inner wall of the second plug 234 is adapted to place and support the lumen tissue.

A detachable structure is between the second plug 234 and the positioning pin.

Preferably, an internal thread is provided at an end of the second plug 234, and the positioning pin is fixed to the second plug 234 by an external thread.

The inner diameter of the second plug 234 is the same as the outer diameter of the hollow rod 231. The second plug 234 is sleeved at the tail of the hollow rod 231. The outer wall of the second plug 234 is provided with a plurality of screw holes, and provided with mating flat bolts, for insertion into the screw holes in the outer wall of the second plug 234, so as to abut closely against the outer wall of the hollow rod 231, and effectuate fixing the second plug 234 with the hollow rod 231.

In the fowarding process of the lumen tissue to the rotary rod 211 by the hollow rod 231, since it is possible to be subjected to certain resistance, it is necessary to perform clamping and fixation. However, in order to facilitate the machining and assembly/disassembly, the first plug 233 is a plastic cover structure having an inner diameter that is slightly smaller than the outer diameter of the hollow rod 231. The first plug 233 may be directly sleeved outside a front end of the hollow rod 231. The first plug 233 is in interference fit with the hollow rod 231 to maintain certain clamping force, which is, however, far less than the second plug 234.

The diameter of the through hole provided in the first plug 233 allowing passage of the rotary rod 211 is slightly smaller than the inner diameter of the hollow rod 231, and larger than the outer diameter of the rotary rod 211 after the biological construct is printed, so as to ensure that the rotary rod of the printed biological construct can enter the hollow rod 231 from the first plug 233.

The lumen tissue and the hollow rod 231 should maintain consistent in length, to avoid the circumstance that the lumen tissue is too long to mount the first plug 233, or the lumen tissue is so short that the lumen tissue slides within the hollow rod 231. At the same time, the biological construct printed on the rotary rod 211 is required to maintain cooperative with the lumen tissue in length.

Furthermore, the lumen tissue and the hollow rod 231 maintain consistent in length, to facilitate cooperative use of the rotary rod 211 mating with the hollow rod 231, for example, to prop up the elastic film for satisfactory attachment to the inner wall of the lumen tissue, and to further facilitate effectuating accurate printing and positioning.

In some embodiments, a gripping slit 235 is provided at an end of the hollow rod 231 adjacent to the rotary rod 211, so as to facilitate gripping the lumen tissue within the hollow rod 231 by a gripping tool through the gripping slit 235.

Further, a through groove is also provided in the cylinder wall of the first plug 233 as a gripping slit.

In some embodiments, the butt-jointed part 23 includes a displacement mechanism 232 for driving the hollow rod 231 to move relative to the rotary rod 211.

In some embodiments, the displacement mechanism 232 includes a mechanical arm 236.

In some embodiments, the operation method of the device for printing lumen tissue construct is as follows:

The lumen tissue is placed into the hollow rod 231, and the first plug 233 and the second plug 234 are respectively mounted, to ensure that the lumen tissue is placed in an annular space between the positioning pin of the second plug and the inner wall of the second plug 234.

The bio-ink is printed on the rotary rod 211, and after it is solidified into a biological construct, the hollow rod 231 is moved toward the rotary rod 211, and the rotary rod 211 is passed through the through hole of the first plug 233 so as to enter the hollow rod 231. At this time, since the lumen tissue may be in friction with surface of the biological construct, certain resistance is generated, so that the second plug 234 has to maintain a stable connection to provide a thrust to the lumen tissue construct.

The elastic film is inflated, so that the elastic film is propped up and the biological construct is attached to the inside of the lumen tissue. Then, the hollow rod 231 is pulled out. Since the first plug 233 can resist the lumen tissue, the lumen tissue may be resisted by the first plug 233, so as to remain within the hollow rod 231. Finally, the first plug 233 is removed, and then tweezers are used to clamp and remove the lumen tissue whose inner wall is attached with the biological construct (lumen tissue construct) from the hollow rod 231.

In some embodiments, the device for printing lumen tissue construct further includes an optical probe for detecting the flatness of an inner wall of the biological construct.

In some embodiments, the lumen tissue construct may be removed directly and then entirely moved such as to be sleeved on a fixed optical probe. That is, the optical probe is stationary, and the lumen tissue moves relative to the optical probe to achieve the purpose of detecting the flatness of the inner wall of the biological construct.

In some embodiments, the optical probe is movably disposed within the rotary rod 211 or the hollow rod 231.

In some embodiments, the optical probe is fixedly disposed within the hollow rod 231.

In some embodiments, the device for printing lumen tissue construct further includes a storage module for loading, cleaning, and storing the lumen tissue construct.

The lumen tissue construct may be removed directly and placed into the storage module.

In some embodiments, the storage module includes a liquid buffer pool into which the lumen tissue construct enters, such that the biological construct attached to its inner wall may not be damaged (e.g. coming off, dead, and the like) due to impact.

Alternatively, the storage module further includes a cleaning pool, such that the lumen tissue construct may be placed into the cleaning pool so as to be cleaned, before moving into the liquid buffer pool for storage.

In an improved embodiment of the device for printing lumen tissue construct of the present disclosure, as shown in FIGS. 2 and 3, the spray head assembly 1 includes a medical adhesive spray head 11, the medical adhesive spray head 11 including a medical adhesive container 111 and a medical adhesive nozzle 112, wherein the medical adhesive container 111 is adapted to contain a medical adhesive, the medical adhesive nozzle 112 is directly connected with the medical adhesive container 111, a top of the medical adhesive container 111 is connected with an air pump through an air path, in which a vacuum generator is provided for generating a negative pressure for the medical adhesive container 111 in a non-printing state. Since the medical adhesive presents an excellent fluidity under certain temperature, in a non-printing state, due to the effect of gravity, the medical adhesive may also drip slowly. Thus, a vacuum generator is added in the air path, where certain negative pressure is present in a non-printing state, and the negative pressure counteracts with the gravity so that the medical adhesive no longer drips freely. Specifically or further, as shown in FIG. 3, a top of the medical adhesive container 111 is provided with a medical adhesive piston 113 which is connected with the air pump through an air path. The air pump is pressurized to extrude the medical adhesive from an ink bladder, and the vacuum generator is located between the air pump and the medical adhesive piston 113.

In an improved embodiment of the device for printing lumen tissue construct of the present disclosure, as shown in FIGS. 2 to 4, the spray head assembly 1 includes a bio-ink spray head 12, which includes a screw pump 121, a bio-ink nozzle 122, and a bio-ink container 125. The bio-ink container 125 is adapted to contain bio-ink (bio-ink). The outlet at the bottom of the bio-ink container 125 communicates with the bio-ink inlet 128 of the screw pump 121 through the connecting tube 127 and the inlet connecting piece 1213. The top of the bio-ink container 125 is provided with a bio-ink piston 124 which is connected with the air pump through an air path. The air pump is pressurized to extrude the bio-ink from the bio-ink container 125 into the screw pump 121. The screw pump 121 includes a spiral stator 1211 and a spiral rotor 1212 for extruding a bio-ink entering the screw pump 121 to the bio-ink nozzle 122, wherein the spiral stator 1211 is made from a silicone material.

Due to the physical properties of the bio-ink, when it is very small at the outlet of the bio-ink container 125, the bio-ink cannot be extruded and may form an accumulation at the outlet. Even if the pressure is increased, the bio-ink which is crushed cannot be extruded. Likewise, even if such means as angular design is performed at the outlet of the bio-ink container 125, the bio-ink cannot be extruded. However, the printing requirement defines that the bio-ink cannot be extruded in large quantities, and only a few amount can be extruded at a time. Therefore, the bio-bricks can only be conveyed from the bio-ink container 125 to the screw pump 121 and extruded by the screw pump 121. As the outlet of the screw pump 121 itself is very large, and the amount of the bio-bricks extruded each time is still greater than the operational requirement, a bio-ink nozzle 122 is provided at the outlet of the screw pump 121.

As shown in FIG. 4, the spiral stator 1211 cannot rotate, the spiral rotor 1212 rotates relative to the spiral stator 1211, and the groove on the spiral rotor 1212 forms a chamber in which only a few amount of bio-bricks can be loaded within each chamber. The bio-bricks are conveyed out to the bio-ink nozzle 122 along with rotation of the spiral rotor 1212. Due to the physical properties of the current bio-ink materials, printing needs to be performed at a low temperature (e.g. 4° C.). The screw stators within the existing screw pumps all use a rubber material, which may rapidly age at a low temperature, so that black powder appears during the printing. The present disclosure makes a modification by making the spiral stator 1211 from silicone, thus avoiding the problem that black powder appears during the printing.

In order to avoid the phenomenon of "hanging droplets" appearing at a front end outlet (a circled portion in FIG. 5) of the bio-ink nozzle 122 when the bio-ink is print (i.e., as the viscosity of the bio-ink is very large, the bio-ink after being extruded may not drip directly, but hang at the nozzle outlet. When a following bio-ink is extruded, a previous bio-ink that does not drip is piled up with the later to become a large droplet hanging at the outlet of the nozzle which may drip when the gravity of such large droplet is greater than the frictional force). In an improved embodiment, on one hand, as shown in FIGS. 5 and 6, a printing outlet end of the bio-ink nozzle 122 has a chamfer, which has a chamfered surface defining an included angle of 10° to 30° with a center line of a printing outlet of the bio-ink nozzle 122. Even further, the included angle is 20°, so that such design can effectively avoid the phenomenon of "hanging droplets". On the other end, an outer surface at the printing outlet end of the bio-ink nozzle 122 has a roughness Ra≤0.4. The outer surface of the bio-ink nozzle 122 may be plated/polished so as to increase the surface smoothness, and be able to better avoid the phenomenon of "hanging droplets".

Figure 12:
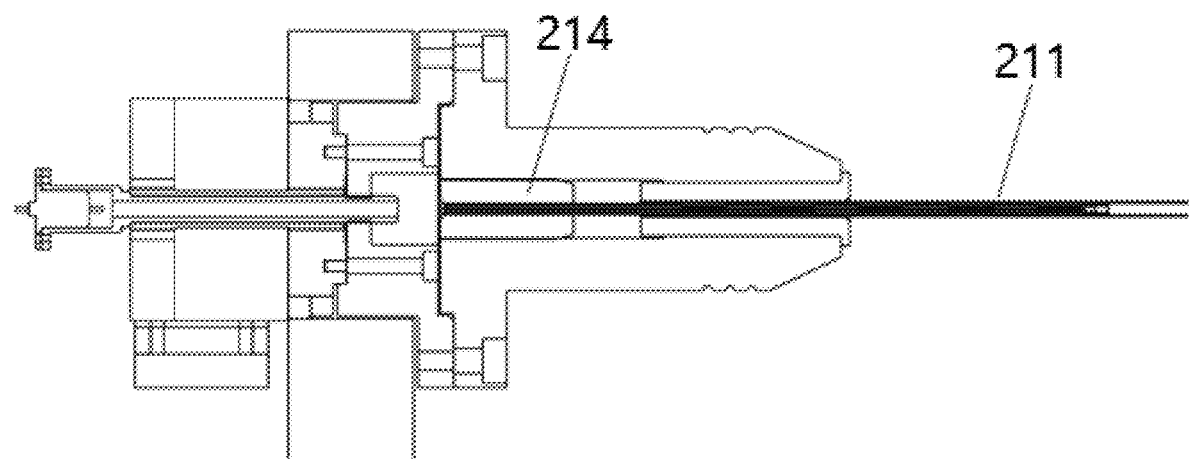
FIG. 12 is a schematic view of an interior structure of a rotary part in the device for printing lumen tissue construct provided by some embodiments of the present disclosure.

Since the currently used bio-ink may tend to coagulate in the case of a temperature greater than 4° C., it is necessary to maintain the bio-ink spray head at an ambient temperature of 4° C. In some improved embodiments, as shown in FIG. 3, the bio-ink spray head 12 also includes a semiconductor cooling plate 126 located behind the screw pump 121 and the bio-ink container 125, which can cool the bio-ink spray head 12 by heat conduction. Further, as shown in FIG. 3, the bio-ink nozzle 122 is externally provided with a thermal insulation sleeve 129. There is certain gap between the thermal insulation sleeve 129 and an exterior of the bio-ink nozzle 122, so that an air thermal insulation layer can be formed. Further, as shown in FIG. 2, the screw pump 121 and the bio-ink container 125 are externally sleeved with a thermal insulation shell 123 including a box cover and thermal insulation cotton covered on the outer surface of the box cover. The thermal insulation can further improve the thermal insulation effect, and reduce the heat exchange between the spray head and the environment. The box cover is provided with a transparent window, for observing a containing condition of the bio-ink within the bio-ink container 125.

In some improved embodiments, the device for printing lumen tissue construct further includes a displacement assembly for moving the spray head assembly 1, and an entirety of the spray head assembly 1 (the bio-ink spray head 12 and the medical adhesive spray head 11) may be displaced in a vertical direction and a horizontal direction, and the medical adhesive spray head 11 may be lifted independently. When the spray head assembly 1 is in the initial state, the horizontal position at the outlet of the bio-ink spray head 12 is located below the horizontal position at the outlet of the medical adhesive spray head 11. After the displacement assembly lowers the spray head assembly 1 to certain height during the printing, the bio-ink spray head 12 extrudes the bio-ink, and wholly ascends a segment after the printing of the lumen tissue is accomplished, before the medical adhesive spray spray head 11 descends independently, to print the medical adhesive.

In an improved embodiment of the device for printing lumen tissue construct of the present disclosure, as shown in FIGS. 7 and 8, the bioprinting platform 2 includes a platform base, a rotary part 21 and a butt-jointed part 23 movable relative to the rotary part 21, wherein the rotary part 21 includes a rotary rod 211 for carrying the bio-ink and the medical adhesive to form a biological construct, and the butt-jointed part 23 includes a hollow rod 231 having an outer wall for carrying the lumen tissue and a displacement mechanism 232. The inner cavity is adapted to contain the rotary rod 211 and the biological construct.

After the biological construct is manufactured by the rotary rod 211, the hollow rod 231 is displaced toward a direction of the rotary part 21 by the displacement mechanism 232. The rotary rod 211 and the biological construct enter the inner cavity of the hollow rod 231, and the lumen tissue sleeved outside the hollow rod 231 is displaced to the outside of the biological construct along with the hollow rod 231. Further, the surface of the hollow rod 231 is plated with a Teflon layer, which is capable of avoiding that the medical adhesive contacts and reacts with the metal surface. The hollow rod 231 is further displaced in an opposite direction by the displacement mechanism 232, and the lumen tissue is removed from the hollow rod 231, and then sleeved on the outer surface of the biological construct, so that the assembly is accomplished to obtain a lumen tissue construct. Further, the outer wall of the rotary rod 211 is covered with an elastic film. During the printing of the biological construct, the elastic film presents a natural state, i.e. covered at the surface of the rotary rod 211. The bio-ink makes up a biological construct at the surface of the elastic film, thereby facilitating better attaching the biological construct to the inner wall of the lumen tissue when the elastic film is propped up.

Further, as shown in FIG. 9, the rotary rod 211 is hollow, and a vent communicating with the inside of the rotary rod 211 is provided on the outer wall of the rotary rod 211 to exhaust air inside the rotary rod 211 to expand the elastic film. During the assembly of the biological construct and the lumen tissue, the rotary rod 211 is internally ventilated so that air expands outwards from the air outlet to prop up the elastic film (conceivably a balloon is blown up). The biological construct at the surface of the elastic film is displaced outwards along with the expansion of the elastic film, and finally in contact with the inner wall of the lumen tissue and adhered onto the inner wall of the lumen tissue, to obtain an artificial tissue precursor. It is demonstrated in practice that, the embodiment is easy to operate and implement, and presents high implementability. Specifically or further, as shown in FIG. 12, a sealing ring 214 is provided inside the rotary part 21. The rotary rod 211 is detachably connected with the sealing ring 214, and the function of the sealing ring 214 is to seal the inner cavity of the rotary rod, so that the process of propping up the elastic film by inflation is more controllable.

As an improvement to the above embodiment, as shown in FIGS. 10 and 11, the interior of the rotary rod 211 is further provided with a heating member 212. The heating member 212 can accelerate the coagulation rate of the bio-ink and shorten the preparation time of the bio-construct. The heating member 212 needs to maintain the surface temperature of the rotary rod at 37-38° C. Further, as shown in FIG. 11, a temperature detecting member 213 is provided at an end of the heating member 212 adjacent to the butt-jointed part 23, for detecting a temperature of the heating member 212, so as to maintain the surface temperature of the rotary rod in real time.

In a specific or improved embodiment, as shown in FIGS. 10 and 11, the heating member 212 includes a heating section 2121 and a spacing section 2123 that are spacedly arranged, wherein a connecting groove 2122 is opened on the surface of the spacing section 2123, and the surface of the heating section 2121 is wound with a resistance wire, the surface of the spacing section 2123 is not wound with a resistance wire, the resistance wire between adjacent heating sections 2121 passes through the connecting groove 2122, and the diameter of the heating section 2121 is smaller than that of the spacing section 2123. The heating member 212 is in clearance fit with the rotary rod 211, and the outer wall of the spacing section 2123 is in contact with the inner wall of the rotary rod 211. The purpose of providing the spacing section is to protect the resistance wire when the heating member 212 is inserted into the rotary rod 211, so as to avoid that the resistance wire is damaged during the assembly.

Figure 14:
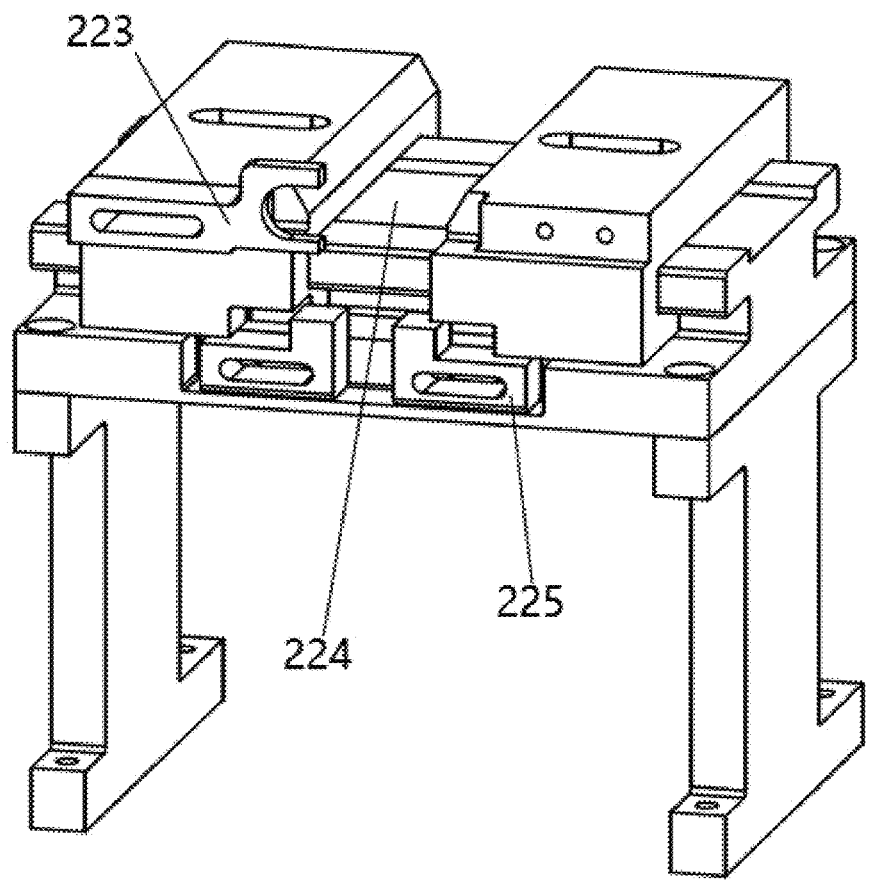
FIG. 14 is a schematic view of the structure of a first embodiment of a gripping mechanism in the device for printing lumen tissue construct provided by some embodiments of the present disclosure from another perspective.
Figure 15:
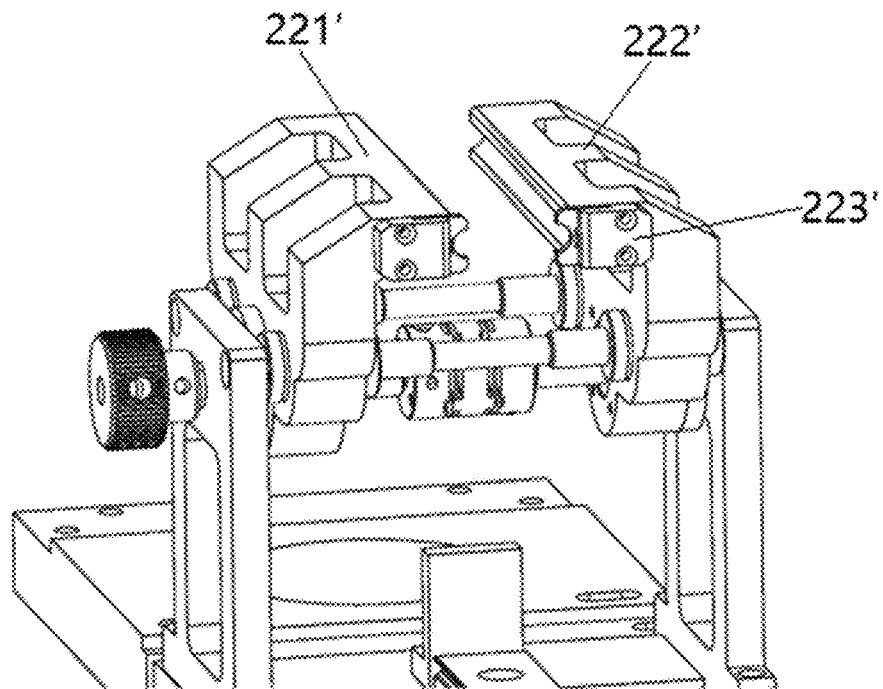
FIG. 15 is a schematic view of the structure of a second embodiment of a gripping mechanism in the device for printing lumen tissue construct provided by some embodiments of the present disclosure.

Regarding how to remove the lumen tissue from the hollow rod 231, in one improved embodiment, as shown in FIGS. 14 and 15, the device for printing lumen tissue construct further includes a retaining member 223, 223' for acting on a tail end of the lumen tissue so that the lumen tissue is disengaged from the hollow rod 231, and the lumen tissue is retained at a periphery of the biological construct on the rotary rod 211, during a process of disengaging the hollow rod 231 from the rotary rod 211.

As shown in FIG. 19, the device for printing lumen tissue construct includes a retaining ring 237 movably disposed at the hollow rod 231 and located at the tail end of the lumen tissue.

The inner diameter of the retaining ring 237 is slightly larger than the outer diameter of the hollow rod 231, and smaller than the outer diameter of the lumen tissue, so as to facilitate the movement of the retaining ring 237 relative to the hollow rod 231. The outer diameter of the retaining ring 237 is larger than that of the lumen tissue.

In the disengagement process of the hollow rod 231 from the rotary rod 211, the retaining ring 237 is adapted to cooperate with the retaining member 223 to limit a position, such that the retaining member 223 restricts the retaining ring 237 from moving along with the hollow rod 231, and the retaining ring 237 restricts the lumen tissue from moving along with the hollow rod 231. Thus, the lumen tissue may be retained at a periphery of the biological construct on the rotary rod 211.

In one improved embodiment, the bioprinting platform 2 further includes a gripping mechanism 22 for gripping the lumen tissue to support and locate the lumen tissue, so as to attach the lumen tissue to the biological construct.

Figure 13:
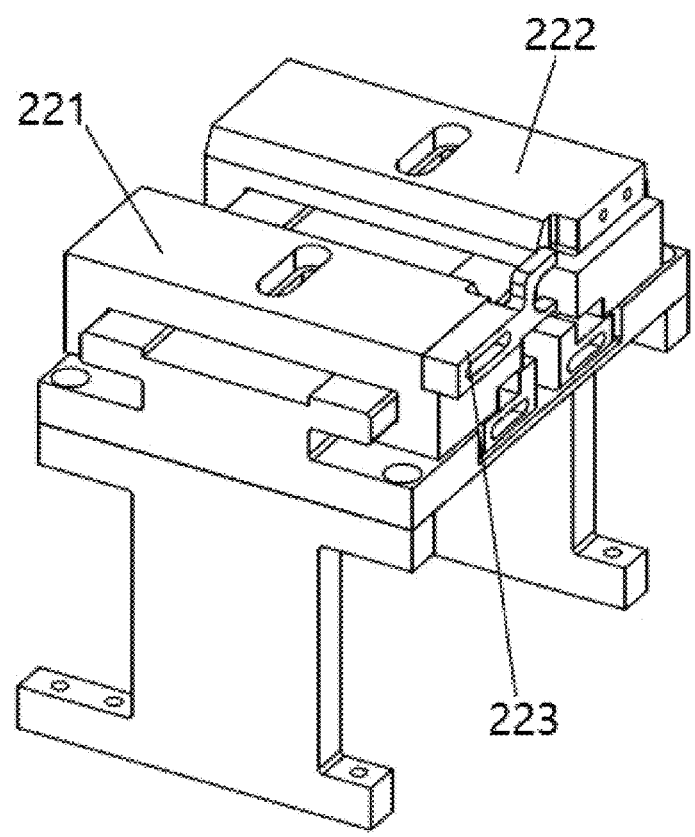
FIG. 13 is a schematic view of the structure of a first embodiment of a gripping mechanism in the device for printing lumen tissue construct provided by some embodiments of the present disclosure.
Figure 16:
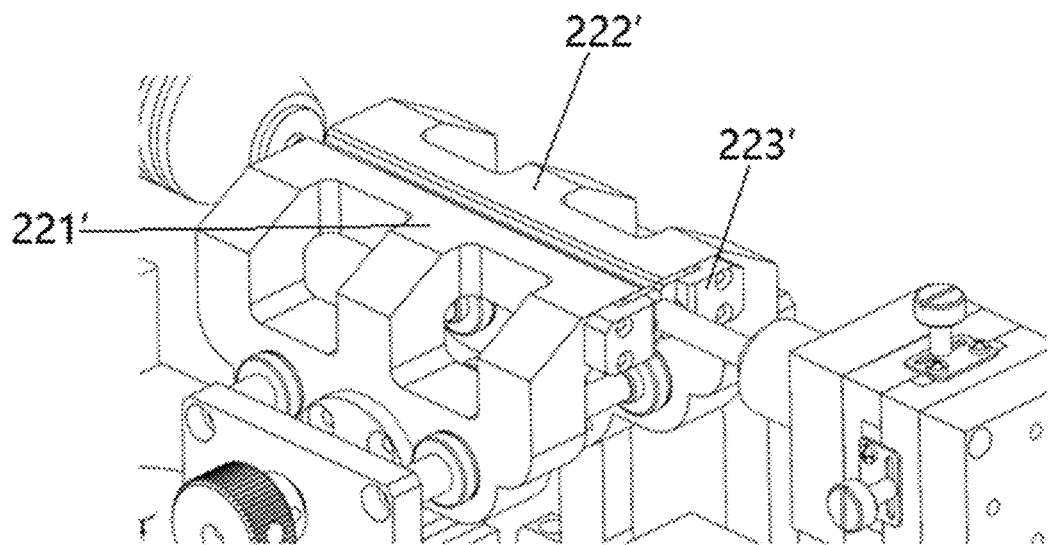
FIG. 16 is a schematic view of the structure of a second embodiment of a gripping mechanism when gripping the lumen tissue in the device for printing lumen tissue construct provided by some embodiments of the present disclosure.

Specifically or further, as shown in FIGS. 13-16, the gripping mechanism 22 includes a first gripping block 221, 221' and a second gripping block 222, 222' which are movable with respect to each other. As shown in FIGS. 13 and 14, the relative movement of the first gripping block 221 and the second gripping block 222 may be preferably realized by providing a guide rail. As shown in FIGS. 15 and 16, the relative movement of the first gripping block 221' and the second gripping block 222' may also be preferably realized by providing a screw nut mechanism. Even further, as shown in FIG. 14, the gripping mechanism 22 further includes a limiting block 225 provided at the bottoms of the first gripping block 221 and the second gripping block 222, for limiting relative movement of the first gripping block 221 and the second gripping block 222, so that the first gripping block 221 and the second gripping block 222 are tangent to the outer wall of the lumen tissue, and it is possible to produce certain limiting effect for the lumen tissue in the process of assembling the lumen tissue construct.

In order to ensure that the lumen tissue is removed from the hollow rod 231 as much as possible, in one further embodiment, as shown in FIGS. 13 to 16, the gripping mechanism 22 further includes a retaining member 223, 223' for acting on a tail end of the lumen tissue so that it is disengaged from the hollow rod 231 to prevent the lumen tissue from following the hollow rod 231 when the hollow rod 231 is displaced in an opposite direction. The retaining members 223, 223' may be disposed at a tail end of the first gripping blocks 221, 221' and/or the second gripping blocks 222, 222', and may also be directly disposed on the gripping mechanism independent of the first gripping block and the second gripping block. Even further, the retaining member 223 is cooperatively provided with a retaining ring acting on the tail end of the lumen tissue, so that the lumen tissue is more easily disengaged from the hollow rod 231. Still further, as shown in FIG. 14, the gripping mechanism 22 further includes a support platform 224 provided at the bottoms of the first gripping block 221 and the second gripping block 222 to support the lumen tissue. In the process of butt-jointing the lumen tissue and the biological construct, the support platform 224 is exactly tangent to the outer wall at the bottom of the lumen tissue, providing an upward force for the lumen tissue and avoiding the sinking of the lumen tissue.

In an improved embodiment of the device for printing lumen tissue construct of the present disclosure, the device for printing lumen tissue construct further includes a reservoir provided below the rotary rod 211, for carrying a lumen tissue construct disengaged and falling from the gripping member 22. After the printing assembly is completed, the lumen tissue construct is gripped by the gripping mechanism 22, and an entirety of the rotary rod 211 is withdrawn towards an opposite direction. The lumen tissue construct is located immediately above the reservoir, and is supported by the gripping mechanism 22. At this time, the gripping mechanism 22 withdraws the gripping force, so that the lumen tissue construct falls vertically into the reservoir. This design can avoid the introduction of new contamination in the transfer operation process implemented manually or by robotic arm after the completion of printing, or the damage caused for printing the inner wall of a blood vessel due to inappropriate operation in the operational process, and facilitate the packaging of a finished product. The present disclosure correspondingly provides a printing method of the aforementioned lumen tissue construct printing device, which includes a step of covering a layer of elastic film on the outer wall of the rotary rod 211 before printing the biological construct. During the printing of the biological construct, the elastic film presents a natural state, i.e. covered at the surface of the rotary rod 211. The bio-ink makes up a biological construct at the surface of the elastic film, thus favorable for removing the biological construct. Further, the printing method of the device for printing lumen tissue construct further includes a film prop-up step: aerating into the elastic film to prop up the elastic film so that the biological construct is attached to the inner wall of the lumen tissue, after the lumen tissue is sleeved outside the biological construct. The biological construct at the surface of the elastic film is displaced outwards along with the expansion of the elastic film, and finally in contact with the inner wall of the lumen tissue and adhered onto the inner wall of the lumen tissue, so that the biological construct is completely evenly, intactly, and flatly attached on the inner wall of the lumen tissue, such as to obtain a lumen tissue construct. It is demonstrated in practice that, the embodiment is easy to operate and implement, and presents a high implementability.

Next, the construction process of the lumen tissue construct of the device for printing lumen tissue construct of the present disclosure is explained by exemplifying the embodiments shown in FIGS. 1 to 14 as follows:

The bio-ink constructs a biological construct on the surface of the elastic film by means of the bio-ink spray head 12, and then a medical adhesive layer for adhering the bio-ink and the lumen tissue is uniformly extruded on the surface of the biological construct by means of the medical adhesive spray head 11.

After the biological construct is made, the hollow rod 231 moves toward the rotary rod 211 until the hollow rod 231 is completely sleeved outside the rotary rod 211. At this time, the lumen tissue is completely outside the biological construct, and the hollow rod 231 moves towards a direction away from the rotary rod 211, when the gripping mechanism 22 prevents the lumen tissue from following the movement of the hollow rod 231. Finally, the hollow rod 231 is completely separated from the rotary rod 211, but the lumen tissue remains outside the biological construct. Limited by the mechanical structure, there is necessarily a gap between the lumen tissue and the biological construct at this time, when an upward force is provided to the lumen tissue by means of the support platform 224, so as to avoid uneven attachment between the biological construct and the artificial blood vessel resulting from a downward movement due to the effect of gravity. Then, the rotary rod 211 is internally ventilated to prop up the elastic film, so that the biological construct is completely attached onto the inner wall of the lumen tissue. The temperature regulating member regulates a temperature to facilitate moulding the biological construct as soon as possible, to finally obtain a lumen tissue construct, which is removed from the rotary rod 211.

Since the printed lumen tissue construct needs to detect the flatness of its inner wall, in an improved embodiment of the device for printing lumen tissue construct of the present disclosure, the device for printing lumen tissue construct may further comprise an optical probe movable inside the rotary rod 211, for detecting a flatness of the inner wall of the biological construct, wherein the rotary rod 211 is made from a transparent material. There is a high implementability to design the optical probe in such a form as to be movable inside the rotary rod 211, and to move the optical probe and photograph the internal wall of the biological construct by an image acquisition software before the lumen tissue construct is removed from the rotary rod 211, so as to judge whether the printed bio-ink coating is intact, smooth and flat, and adequately utilize the hollow structure inside the rotary rod 211 to improve the structural utilization rate.

For how to effectuate that the optical probe is movable inside the rotary rod 211, in some improved embodiments, the optical probe is fixedly disposed within the hollow rod 231. For example, the hollow rod 231 is designed in a double-layer embedded structure, in which the first layer is adapted to embedding an artificial blood vessel, and the front end of the second layer is provided with an optical probe. The rotary rod 211 may also be a double-layer structure, in which ventilation is performed within the sandwich for propping up the elastic film. The elastic film only covers the surface of the rotary rod 211 but does not cover the front end, such as to enable the optical probe to extend into the rotary rod 211. In the assembly process, the lumen tissue is sleeved on the surface of the biological construct, and the optical probe also moves along with the hollow rod 231 to the furthest end of the biological construct. When the lumen tissue is removed, the optical probe also moves along with the hollow rod 231 to the foremost end of the artificial precursor tissue, so as to accomplish the flatness detection in the assembly process. Certainly, in other improved embodiments, the optical probe is movably disposed within the hollow rod 231, that is, the optical probe moves independently with respect to the hollow rod 231, and the flatness detection can also be accomplished. In some other modified embodiments, the optical probe is movably disposed within the rotary rod 211, and the optical probe moves from an end to the other within the rotary rod 211 to accomplish the flatness detection.

The present disclosure further provides a 3D bioprinter, which includes the aforementioned lumen tissue construct printing device. As the device for printing lumen tissue construct of the present disclosure can improve the biological reliability of the lumen tissue, correspondingly, the 3D bioprinter of the present disclosure also has the advantageous technical effects described above, and thus will no longer be repeated here.

The bio-ink in the present disclosure includes a bio-brick, as well as other substances for regulating the performance of the bio-brick.

The bio-brick (please see CN106039419B) includes: a cell, a core layer enveloping the cell, and a shell encapsulating the core layer, wherein the core layer and the shell layer are each independently made from a biodegradable material. The biodegradable materials in the core layer and the shell layer can reduce or avoid that the cells within the bio-brick suffers (e.g., bioprinting) from mechanical damage in the operation process, and can provide controlled release of substances (e.g., nutrients, extracellular matrices, cytokines, active substances of drugs), so as to promote cellular activity and function (proliferation, differentiation, migration, secretion or metabolism).

The above-combined embodiments make detailed explanations for the embodiments of the present disclosure, but the present disclosure is not limited to the embodiments described. For a person skilled in the art, multiple changes, modifications, equivalent replacements, and variations made to such embodiments still fall within the protection scope of the present disclosure without departing from the principles and substantive spirit of the present disclosure.

What is claimed is:

1. A device for printing lumen tissue construct, comprising:
   a spray head assembly for printing a biological construct; and
   a bioprinting platform for supporting a lumen tissue, and for carrying a biological construct printed by the spray head assembly, and for applying the biological construct printed by the spray head assembly to an inner surface of the lumen tissue, wherein the bioprinting platform comprises:
   a platform base;
   a butt-jointed part, comprising a hollow rod disposed at the platform base, wherein the hollow rod is adapted to carry the lumen tissue; and
   a rotary part, comprising a rotary rod rotatably disposed at the platform base, wherein the rotary rod is configured to carry the biological construct printed by the spray head assembly; and wherein the rotary rod is configured to be insertable into the hollow rod and is configured to apply the biological construct printed by the spray head assembly to the inner surface of the lumen tissue.

2. The device according to claim 1, wherein the spray head assembly comprises:
   a bio-ink container for containing bio-ink;
   a medical adhesive container for containing medical adhesive; and
   a nozzle configured to alternatively communicate with the bio-ink container and the medical adhesive container.

3. The device according to claim 1, wherein the spray head assembly comprises:
   a medical adhesive spray head for applying medical adhesive to a surface of the biological construct; and
   a bio-ink spray head for providing bio-ink to the bioprinting platform so as to print the biological construct.

4. The device according to claim 3, wherein the medical adhesive spray head comprises:
   a medical adhesive container for containing medical adhesive; and
   a medical adhesive nozzle in communication with the medical adhesive container, for applying medical adhesive to the surface of the biological construct.

5. The device according to claim 4, wherein the medical adhesive spray head comprises a medical adhesive piston disposed in the medical adhesive container, wherein medical adhesive piston is adapted to eject the medical adhesive.

6. The device according to claim 3, further comprising a first force applying member for ejecting the medical adhesive from the medical adhesive spray head.

7. The device according to claim 6, wherein the first force applying member comprises a first air pump for providing an air pressure so as to eject the medical adhesive from the medical adhesive spray head; or
   wherein the first force applying member comprises a first plunger pump for providing a thrust so as to eject the medical adhesive from the medical adhesive spray head.

8. The device according to claim 3, wherein the bio-ink spray head comprises:
   a bio-ink container for containing the bio-ink; and
   a bio-ink nozzle in communication with the bio-ink container, for ejecting the bio-ink contained in the bio-ink container so as to print the biological construct.

9. The device according to claim 8, wherein the bio-ink spray head comprises a bio-ink piston disposed in the bio-ink container, wherein the bio-ink piston is adapted to eject the bio-ink contained in the bio-ink container.

10. The device according to claim 8, further comprising a force applying member in communication with the bio-ink container and the bio-ink nozzle, for causing the bio-ink contained in the bio-ink container to flow to the bio-ink nozzle;
    wherein the force applying member comprises:
    a housing in communication with the bio-ink container and the bio-ink nozzle;
    a spiral stator fixedly disposed at an inner wall of the housing; and
    a spiral rotor rotatably disposed within the housing;
    wherein the spiral rotor is configured to cooperate with the spiral stator to supply bio-ink within the housing to the bio-ink nozzle.

11. The device according to claim 3, further comprising a force applying member for ejecting the bio-ink from the bio-ink spray head.

12. The device according to claim 11, wherein the force applying member comprises a plunger pump for providing a thrust to eject the bio-ink from the bio-ink spray head; or
    wherein the force applying member comprises an air pump for providing an air pressure so as to eject the bio-ink from the bio-ink spray head.

13. The device according to claim 1, wherein an outer surface of the rotary rod is covered with an elastic film;
    wherein the rotary rod is hollow, and a vent communicating with an inside of the rotary rod is provided on an outer wall of the rotary rod to exhaust air inside the rotary rod to expand the elastic film.

14. The device according to claim 1, further comprising a temperature regulating assembly for regulating a temperature of the biological construct on the rotary rod.

15. The device according to claim 14, wherein the temperature regulating assembly comprises a heating member disposed inside the rotary rod; or
    wherein the temperature regulating assembly comprises:
    a circulation line, within which there calculatingly flows a refrigerant for adjusting the temperature of the biological construct on the rotary rod; and
    a pump, disposed on the circulation line, for providing power to cause refrigerant to flow within the circulation line.

16. The device according to claim 1, wherein an outer wall of the hollow rod is configured to carry the lumen tissue.

17. The device according to claim 16, further comprising:
    a retaining member, which is adapted to act on a tail end of the lumen tissue so that the lumen tissue is disengaged from the hollow rod, and retained at a periphery of the biological construct on the rotary rod, during a process of disengaging the hollow rod from the rotary rod;
    a retaining ring movably disposed on the hollow rod, wherein the retaining ring is located at the tail end of the lumen tissue, and the retaining ring is adapted to cooperate with the retaining member to retain the lumen tissue at a periphery of the biological construct on the rotary rod.

18. The device according to claim 16, wherein the bioprinting platform further comprises a gripping mechanism for gripping the lumen tissue to support and locate the lumen tissue, so as to attach the lumen tissue to the biological construct;

wherein the gripping mechanism comprises a first gripping block and a second gripping block which are movable with respect to each other.

19. The device according to claim 18, wherein the gripping mechanism further comprises a limiting block disposed at a bottom of the first gripping block and a bottom of the second gripping block, for limiting relative movement of the first gripping block and the second gripping block, so that the first gripping block and the second gripping block are tangent to an outer wall of the lumen tissue;

wherein the gripping mechanism further comprises a support platform disposed at the bottom of the first gripping block and the bottom of the second gripping block to support the lumen tissue.

20. The device according to claim 1, wherein the hollow rod is configured to carry the lumen tissue therein; the rotary rod is configured to be insertable into the hollow rod, and located within the lumen tissue, so as to apply the biological construct carried thereon to the inner surface of the lumen tissue.

21. The device according to claim 20, wherein a first plug is provided at a first end of the hollow rod adjacent to the rotary rod, wherein the first plug is provided with a through hole for allowing passage of the rotary rod; and a second plug is provided at a second end of the hollow rod far away from the rotary rod;

wherein the second plug is provided with a positioning pin, wherein an annular cavity between the positioning pin and the hollow rod is adapted to position the lumen tissue;

wherein a gripping slit is provided at the first end of the hollow rod adjacent to the rotary rod, so as to facilitate gripping the lumen tissue within the hollow rod by a gripping tool through the gripping slit.

22. A method of printing lumen tissue construct using the device according to claim 1, comprising:

a step of covering a layer of elastic film on an outer wall of the rotary rod before printing the biological construct;

a step of printing the biological construct on an outside of the elastic film;

a step of sleeving the lumen tissue on an outside of the biological construct; and a step of aerating into a space between the elastic film and the rotary rod to expand the elastic film so that the biological construct is attached to an inner wall of the lumen tissue.

* * * * *

UNITED STATES PATENT AND TRADEMARK OFFICE
CERTIFICATE OF CORRECTION

PATENT NO. : 11,311,368 B2
APPLICATION NO. : 16/252253
DATED : April 26, 2022
INVENTOR(S) : Yijun Li et al.

It is certified that error appears in the above-identified patent and that said Letters Patent is hereby corrected as shown below:

On the Title Page

The Foreign Application Priority Data section:
Jan. 18, 2018 (CN) the number "20181048700.6" should read -- 201810048700.6 --.
Jan. 11, 2019 (CN) the number "20191025832.1" should read -- 201910025832.1 --.

In the Claims

Column 24, Claim 15, Line 44, "calculatingly" should read -- circulatingly --.

Signed and Sealed this
Twenty-eighth Day of June, 2022

Katherine Kelly Vidal
*Director of the United States Patent and Trademark Office*